US010780217B2

(12) United States Patent
Nazzaro et al.

(10) Patent No.: US 10,780,217 B2
(45) Date of Patent: Sep. 22, 2020

(54) RATCHET DRIVE FOR ON BODY DELIVERY SYSTEM

(71) Applicant: Insulet Corporation, Acton, MA (US)

(72) Inventors: David Nazzaro, Groveland, MA (US); Simon Kozin, Lexington, MA (US); Maureen McCaffrey, Boston, MA (US)

(73) Assignee: INSULET CORPORATION, Acton, MA (US)

( * ) Notice: Subject to any disclaimer, the term of this patent is extended or adjusted under 35 U.S.C. 154(b) by 401 days.

(21) Appl. No.: 15/809,491

(22) Filed: Nov. 10, 2017

(65) Prior Publication Data

US 2018/0126068 A1    May 10, 2018

Related U.S. Application Data

(60) Provisional application No. 62/439,822, filed on Dec. 28, 2016, provisional application No. 62/420,382, filed on Nov. 10, 2016.

(51) Int. Cl.
*A61M 5/145* (2006.01)
*A61M 5/142* (2006.01)
(Continued)

(52) U.S. Cl.
CPC ...... *A61M 5/1452* (2013.01); *A61M 5/14248* (2013.01); *A61M 5/16804* (2013.01);
(Continued)

(58) Field of Classification Search
CPC ............ A61M 5/14248; A61M 5/1452; A61M 5/16804; A61M 5/31533; A61M 5/31536;
(Continued)

(56) References Cited

U.S. PATENT DOCUMENTS

| 1,441,508 A | 1/1923 | Marius et al. |
| 2,198,666 A | 4/1940 | Gruskin |

(Continued)

FOREIGN PATENT DOCUMENTS

| CA | 606281 A | 10/1960 |
| CN | 1375338 A | 10/2002 |

(Continued)

OTHER PUBLICATIONS

Lind, et al.,"Linear Motion Miniature Actuators." Paper presented at the 2nd Tampere International Conference on Machine Automation, Tampere, Finland (Sep. 15-18, 1998) 2 pages.
Author unknown, "The Animas R-1000 Insulin Pump—Animas Corporation intends to exit the insulin pump business and discontinue the manufacturing and sale of Animas® Vibe® and OneTouch Ping® insulin pumps." [online], Dec. 1999 [retrieved on Oct. 16, 2018]. Retrieved from the Internet URL: http://www.animaspatientsupport.com/.
(Continued)

*Primary Examiner* — Kami A Bosworth
*Assistant Examiner* — Leah J Swanson

(57) ABSTRACT

Ratchet-based drive systems for more reliable and safer drug delivery are provided. The ratchet-based drive systems restrict angular movement and/or linear movement of components that cause a plunger to expel a liquid drug from a drug container. Movement of the components can be restricted to correspond to a predetermined or desired portion of the liquid drug. In the case that control of the drive system is lost or fails, the maximum amount of drug that could be delivered is limited to a known amount, thereby reducing the likelihood of an overdose.

22 Claims, 13 Drawing Sheets

(51) Int. Cl.
*A61M 5/168* (2006.01)
*A61M 5/315* (2006.01)

(52) U.S. Cl.
CPC ..... *A61M 5/16877* (2013.01); *A61M 5/31536* (2013.01); *A61M 5/31546* (2013.01); *A61M 5/31568* (2013.01); *A61M 2005/14533* (2013.01); *A61M 2005/3154* (2013.01)

(58) Field of Classification Search
CPC .... A61M 5/14244; A61M 2005/14533; A61M 2005/3154; A61M 2005/3022
See application file for complete search history.

(56) References Cited

U.S. PATENT DOCUMENTS

| | | |
|---|---|---|
| 3,176,712 A | 4/1965 | Ramsden |
| 3,297,260 A | 1/1967 | Barlow |
| 3,885,662 A | 5/1975 | Schaefer |
| 3,946,732 A | 3/1976 | Hurscham |
| 3,993,061 A | 11/1976 | OLeary |
| 4,108,177 A | 8/1978 | Pistor |
| 4,152,098 A | 5/1979 | Moody et al. |
| 4,210,173 A | 7/1980 | Choksi et al. |
| 4,221,219 A | 9/1980 | Tucker |
| 4,257,324 A | 3/1981 | Stefansson et al. |
| 4,268,150 A | 5/1981 | Chen |
| 4,313,439 A | 2/1982 | Babb et al. |
| 4,417,889 A | 11/1983 | Choi |
| 4,424,720 A | 1/1984 | Bucchianeri |
| 4,435,173 A | 3/1984 | Siposs et al. |
| 4,498,843 A | 2/1985 | Schneider et al. |
| 4,507,115 A | 3/1985 | Kambara et al. |
| 4,551,134 A | 11/1985 | Slavik et al. |
| 4,562,751 A | 1/1986 | Nason et al. |
| 4,567,549 A | 1/1986 | Lemme |
| 4,585,439 A | 4/1986 | Michel |
| 4,601,707 A | 7/1986 | Albisser et al. |
| 4,634,427 A | 1/1987 | Hannula et al. |
| 4,671,429 A | 6/1987 | Spaanderman et al. |
| 4,678,408 A | 7/1987 | Nason et al. |
| 4,684,368 A | 8/1987 | Kenyon |
| 4,685,903 A | 8/1987 | Cable et al. |
| 4,755,169 A | 7/1988 | Sarnoff et al. |
| 4,766,889 A | 8/1988 | Trick et al. |
| 4,808,161 A | 2/1989 | Kamen |
| 4,846,797 A | 7/1989 | Howson et al. |
| 4,858,619 A | 8/1989 | Toth |
| 4,898,579 A | 2/1990 | Groshong et al. |
| 4,908,017 A | 3/1990 | Howson et al. |
| 4,944,659 A | 7/1990 | Labbe et al. |
| 4,969,874 A | 11/1990 | Michel et al. |
| 5,007,458 A | 4/1991 | Marcus et al. |
| 5,020,325 A | 6/1991 | Henault |
| 5,062,841 A | 11/1991 | Siegel |
| 5,178,609 A | 1/1993 | Ishikawa |
| 5,205,819 A | 4/1993 | Ross et al. |
| 5,213,483 A | 5/1993 | Flaherty et al. |
| 5,222,362 A | 6/1993 | Maus et al. |
| 5,236,416 A | 8/1993 | McDaniel et al. |
| 5,261,882 A | 11/1993 | Sealfon |
| 5,261,884 A | 11/1993 | Stern et al. |
| 5,277,338 A | 1/1994 | Divall |
| 5,281,202 A | 1/1994 | Weber et al. |
| 5,346,476 A | 9/1994 | Elson |
| 5,364,342 A | 11/1994 | Beuchat et al. |
| 5,388,615 A | 2/1995 | Edlund et al. |
| 5,433,710 A | 7/1995 | VanAntwerp et al. |
| 5,503,628 A | 4/1996 | Fetters et al. |
| 5,520,661 A | 5/1996 | Lal et al. |
| 5,533,389 A | 7/1996 | Kamen et al. |
| 5,582,593 A | 12/1996 | Hultman |
| 5,618,269 A | 4/1997 | Jacobsen et al. |
| 5,637,095 A | 6/1997 | Nason et al. |
| 5,665,070 A | 9/1997 | McPhee |
| 5,713,875 A | 2/1998 | Tanner, II |
| 5,747,350 A | 5/1998 | Sattler |
| 5,748,827 A | 5/1998 | Holl et al. |
| 5,776,103 A | 7/1998 | Kriesel et al. |
| 5,779,676 A | 7/1998 | Kriesel et al. |
| 5,785,688 A | 7/1998 | Joshi et al. |
| 5,797,881 A | 8/1998 | Gadot |
| 5,800,397 A | 9/1998 | Wilson et al. |
| 5,807,075 A | 9/1998 | Jacobsen et al. |
| 5,839,467 A | 11/1998 | Saaski et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,957,890 A | 9/1999 | Mann et al. |
| 5,961,492 A | 10/1999 | Kriesel et al. |
| 5,971,963 A | 10/1999 | Choi |
| 6,019,747 A | 2/2000 | McPhee |
| 6,050,457 A | 4/2000 | Arnold et al. |
| 6,159,188 A | 12/2000 | Laibovitz et al. |
| 6,174,300 B1 | 1/2001 | Kriesel et al. |
| 6,190,359 B1 | 2/2001 | Heruth |
| 6,200,293 B1 | 3/2001 | Kriesel et al. |
| 6,363,609 B1 | 4/2002 | Pickren |
| 6,375,638 B2 | 4/2002 | Nason et al. |
| 6,474,219 B2 | 11/2002 | Klitmose et al. |
| 6,485,461 B1 | 11/2002 | Mason et al. |
| 6,485,462 B1 | 11/2002 | Kriesel |
| 6,488,652 B1 | 12/2002 | Weijand et al. |
| 6,520,936 B1 | 2/2003 | Mann |
| 6,527,744 B1 | 3/2003 | Kriesel et al. |
| 6,537,249 B2 | 3/2003 | Kriesell et al. |
| 6,569,115 B1 | 5/2003 | Barker et al. |
| 6,595,956 B1 | 7/2003 | Gross et al. |
| 6,656,158 B2 | 12/2003 | Mahoney et al. |
| 6,699,218 B2 | 3/2004 | Flaherty et al. |
| 6,723,072 B2 | 4/2004 | Flaherty et al. |
| 6,749,407 B2 | 6/2004 | Xie et al. |
| 6,851,260 B2 | 2/2005 | Merno |
| 6,883,778 B1 | 4/2005 | Newton et al. |
| 7,018,360 B2 | 3/2006 | Flaherty et al. |
| 7,128,727 B2 | 10/2006 | Flaherty et al. |
| 7,144,384 B2 | 12/2006 | Gorman et al. |
| 7,160,272 B1 | 1/2007 | Eyal et al. |
| 7,771,392 B2 * | 8/2010 | De Polo ............... A61M 5/1452 604/152 |
| 7,914,499 B2 | 3/2011 | Gonnelli et al. |
| 8,382,703 B1 | 2/2013 | Abdelaal |
| 8,499,913 B2 | 8/2013 | Gunter |
| 8,939,935 B2 | 1/2015 | O'Connor et al. |
| 9,180,244 B2 | 11/2015 | Anderson et al. |
| 9,192,716 B2 | 11/2015 | Jugl et al. |
| 9,402,950 B2 | 8/2016 | Dilanni et al. |
| 2001/0016710 A1 | 8/2001 | Nason et al. |
| 2001/0056258 A1 | 12/2001 | Evans |
| 2002/0029018 A1 * | 3/2002 | Jeffrey ............... A61M 5/14232 604/209 |
| 2002/0032374 A1 | 3/2002 | Holker et al. |
| 2002/0037221 A1 | 3/2002 | Mastrangelo et al. |
| 2002/0173769 A1 | 11/2002 | Gray et al. |
| 2002/0173830 A1 | 11/2002 | Starkweather et al. |
| 2003/0040715 A1 | 2/2003 | D'Antonio et al. |
| 2003/0097092 A1 | 5/2003 | Flaherty |
| 2003/0109827 A1 | 6/2003 | Lavi et al. |
| 2003/0163097 A1 | 8/2003 | Fleury et al. |
| 2003/0199825 A1 | 10/2003 | Flaherty |
| 2004/0010207 A1 | 1/2004 | Flaherty et al. |
| 2004/0064088 A1 | 4/2004 | Gorman et al. |
| 2004/0068224 A1 | 4/2004 | Couvillon et al. |
| 2004/0069044 A1 | 4/2004 | Lavi et al. |
| 2004/0092865 A1 | 5/2004 | Flaherty et al. |
| 2004/0094733 A1 | 5/2004 | Hower et al. |
| 2004/0153032 A1 * | 8/2004 | Garribotto ........ A61M 5/14248 604/131 |
| 2005/0020980 A1 | 1/2005 | Inoue et al. |
| 2005/0165363 A1 | 7/2005 | Judson et al. |
| 2005/0203461 A1 | 9/2005 | Flaherty et al. |
| 2005/0238507 A1 | 10/2005 | Dilanni et al. |

(56) References Cited

U.S. PATENT DOCUMENTS

| | | |
|---|---|---|
| 2005/0273059 A1 | 12/2005 | Mernoe et al. |
| 2006/0041229 A1 | 2/2006 | Garibotto et al. |
| 2006/0079765 A1 | 4/2006 | Neer et al. |
| 2006/0155210 A1 | 7/2006 | Beckman et al. |
| 2006/0173439 A1 | 8/2006 | Thorne et al. |
| 2006/0178633 A1 | 8/2006 | Garibotto et al. |
| 2006/0253085 A1 | 11/2006 | Geismar et al. |
| 2006/0282290 A1 | 12/2006 | Flaherty et al. |
| 2007/0005018 A1 | 1/2007 | Tekbuchava |
| 2007/0118405 A1 | 5/2007 | Campbell et al. |
| 2007/0282269 A1 | 12/2007 | Carter et al. |
| 2008/0004515 A1 | 1/2008 | Jennewine |
| 2008/0051738 A1 | 2/2008 | Griffin |
| 2008/0114304 A1 | 5/2008 | Nalesso et al. |
| 2008/0172028 A1 | 7/2008 | Blomquist |
| 2009/0024083 A1 | 1/2009 | Kriesel et al. |
| 2009/0062767 A1 | 3/2009 | Van Antwerp et al. |
| 2009/0198215 A1 | 8/2009 | Chong et al. |
| 2010/0036326 A1 | 2/2010 | Matusch |
| 2010/0152658 A1 | 6/2010 | Hanson et al. |
| 2010/0241066 A1 | 9/2010 | Hansen et al. |
| 2011/0054399 A1 | 3/2011 | Chong et al. |
| 2011/0144586 A1 | 6/2011 | Michaud et al. |
| 2011/0230833 A1 | 9/2011 | Landman et al. |
| 2012/0078161 A1 | 3/2012 | Masterson et al. |
| 2013/0006213 A1 | 1/2013 | Arnitz et al. |
| 2013/0064701 A1 | 3/2013 | Konishi |
| 2013/0178803 A1 | 7/2013 | Raab |
| 2013/0245545 A1 | 9/2013 | Arnold et al. |
| 2013/0267932 A1 | 10/2013 | Franke et al. |
| 2013/0017099 A1 | 12/2013 | Genoud et al. |
| 2014/0018730 A1 | 1/2014 | Muller-Pathle |
| 2014/0127048 A1 | 5/2014 | Dilanni et al. |
| 2014/0128839 A1 | 5/2014 | Dilanni et al. |
| 2014/0142508 A1 | 5/2014 | Dilanni et al. |
| 2014/0148784 A1 | 5/2014 | Anderson et al. |
| 2014/0171901 A1 | 6/2014 | Langsdorf et al. |
| 2015/0041498 A1 | 2/2015 | Kakiuchi et al. |
| 2015/0057613 A1 | 2/2015 | Clemente et al. |
| 2015/0202386 A1 | 7/2015 | Brady et al. |
| 2015/0290389 A1 | 10/2015 | Nessel |
| 2015/0297825 A1 | 10/2015 | Focht et al. |
| 2016/0008549 A1 | 1/2016 | Plumptre et al. |
| 2016/0025544 A1 | 1/2016 | Kamen et al. |
| 2016/0193423 A1 | 7/2016 | Bilton |
| 2017/0021096 A1 | 1/2017 | Cole et al. |
| 2017/0021137 A1 | 1/2017 | Cole |
| 2017/0216516 A1 | 8/2017 | Dale et al. |
| 2017/0239415 A1 | 8/2017 | Hwang et al. |
| 2018/0021521 A1 | 1/2018 | Sanchez et al. |
| 2018/0313346 A1 | 11/2018 | Oakes et al. |

FOREIGN PATENT DOCUMENTS

| | | |
|---|---|---|
| DE | 4200595 A1 | 7/1993 |
| DE | 19723648 C1 | 8/1998 |
| EP | 0454331 A1 | 10/1991 |
| EP | 0789146 A1 | 8/1997 |
| EP | 0867196 A2 | 9/1998 |
| EP | 1065378 A2 | 1/2001 |
| EP | 1177802 A1 | 2/2002 |
| EP | 1403519 A1 | 3/2004 |
| EP | 2397181 A1 | 12/2011 |
| EP | 2468338 A1 | 6/2012 |
| EP | 2703024 A1 | 3/2014 |
| FR | 2096275 A5 | 2/1972 |
| FR | 2455269 A1 | 11/1980 |
| FR | 2507637 A1 | 12/1982 |
| FR | 2731475 A1 | 9/1996 |
| GB | 357139 A | 9/1931 |
| GB | 810488 A | 3/1959 |
| GB | 875034 A | 8/1961 |
| GB | 1204836 A | 9/1970 |
| GB | 2008806 A | 6/1979 |
| GB | 2077367 A | 12/1981 |
| GB | 2456681 A | 7/2009 |
| GB | 2549750 A | 11/2017 |
| IL | 46017 A | 11/1977 |
| JP | 06063133 A | 3/1994 |
| JP | H08238324 A | 9/1996 |
| JP | 2004247271 A | 9/2004 |
| JP | 2004274719 A | 9/2004 |
| JP | 2005188355 A | 7/2005 |
| JP | 2006159228 A | 6/2006 |
| JP | 2006249130 A | 9/2006 |
| NL | 1019126 C1 | 4/2003 |
| WO | 8101658 A1 | 6/1981 |
| WO | 8606796 A1 | 11/1986 |
| WO | 9415660 A1 | 7/1994 |
| WO | 9855073 A1 | 12/1998 |
| WO | 9856293 A1 | 12/1998 |
| WO | 9910040 A1 | 3/1999 |
| WO | 9910049 A1 | 3/1999 |
| WO | 9962576 A1 | 12/1999 |
| WO | 0029047 A1 | 5/2000 |
| WO | 200178812 A1 | 10/2001 |
| WO | 0220073 A2 | 3/2002 |
| WO | 200226282 A2 | 4/2002 |
| WO | 02068823 A1 | 9/2002 |
| WO | 2002076535 A1 | 10/2002 |
| WO | 2003097133 A1 | 11/2003 |
| WO | 2004056412 A2 | 7/2004 |
| WO | 2004110526 A1 | 12/2004 |
| WO | 2007066152 A2 | 6/2007 |
| WO | 2008133702 A1 | 11/2008 |
| WO | 2009039203 A2 | 3/2009 |
| WO | 2010139793 A1 | 12/2010 |
| WO | 2011075042 A1 | 6/2011 |
| WO | 2011133823 A1 | 6/2011 |
| WO | 2012073032 A1 | 6/2012 |
| WO | 2013050535 A2 | 4/2013 |
| WO | 2013137893 A1 | 9/2013 |
| WO | 2013149186 A1 | 10/2013 |
| WO | 2014149357 A1 | 9/2014 |
| WO | 2015032772 A1 | 3/2015 |
| WO | 2015081337 A2 | 6/2015 |
| WO | 2015117854 A1 | 8/2015 |
| WO | 2015167201 A1 | 11/2015 |
| WO | 2015177082 A1 | 11/2015 |
| WO | 2017187177 A1 | 11/2017 |

OTHER PUBLICATIONS

Author unknown, CeramTec "Discover the Electro Ceramic Products CeramTec acquired from Morgan Advanced Materials" [online], Mar. 1, 2001 [retrieved on Oct. 17, 2018]. Retrieved from the Internet URL: http://www.morgantechnicalceramics.com/, 2 pages.
Vaughan, M.E., "The Design, Fabrication, and Modeling of a Piezoelectric Linear Motor." Master's thesis, Virginia Polytechnic Institute and State University, VA. (2001).
Galante, et al., "Design, Modeling, and Performance of a High Force Piezoelectric Inchworm Motor," Journal of Intelligent Material Systems and Structures, vol. 10, 962-972 (1999).
International Search Report and Written Opinion for application No. PCT/US17/46508 dated Jan. 17, 2018, 14 pages.
International Search Report and Written Opinion for application No. PCT/US17/46777, dated Dec. 13, 2017, 14 pages.
International Search Report and Written Opinion for application No. PCT/US17/46737, dated Dec. 14, 2017, 11 pages.
International Search Report and Written Opinion for application No. PCT/US17/55054, dated Jan. 25, 2018, 13 pages.
International Search Report and Written Opinion for application No. PCT/US2018/014351, dated Jun. 4, 2018, 11 pages.
International Search Report and Written Opinion for application No. PCT/US18/45155, dated Oct. 15, 2018, 15 pages.
International Search Report and Written Opinion for application No. PCT/US17/34814, dated Oct. 11, 2017, 16 pages.
European Search Report and Written Opinion for the European Patent Application No. EP19177571, dated Oct. 30, 2019, 8 pages.
International Preliminary Report on Patentability for the International Patent Application No. PCT/US18/14351, dated Aug. 1, 2019, 7 pages.

(56) References Cited

OTHER PUBLICATIONS

International Preliminary Report on Patentability for the International Patent Application No. PCT/US2017/046777, dated Feb. 19, 2019, 8 pages.
International Preliminary Report on Patentability for the International Patent Application No. PCT/US2017/046737, dated Feb. 19, 2019, 8 pages.
International Preliminary Report on Patentability for the International Patent Application No. PCT/US2017/046508, dated Feb. 12, 2019, 10 pages.
International Preliminary Report on Patentability for the International Patent Application No. PCT/US2017/055054, dated Apr. 9, 2019, 8 pages.
International Search Report and Written Opinion for application No. PCT/US2017/034811, dated Oct. 18, 2017, 15 pages.
EPO Search Report dated Nov. 11, 2015, received in corresponding Application No. 13768938.6, 7 pgs.
PCT International Search Report and Written Opinion dated Aug. 6, 2013, received in corresponding PCT Application No. PCT/US13/34674, pp. 1-19.
International Search Report and Written Opinion for International application No. PCT/GB2007/004073, dated Jan. 31, 2008.
International Search Report and Written Opinion for the International Patent Application No. PCT/US2019/063615, dated May 3, 2020, 16 pages.
International Preliminary Report on Patentability for the International Patent Application No. PCT/US2018/045155, dated Feb. 13, 2020, 10 pages.
International Search Report and Written Opinion for the International Patent Application No. PCT/US2019/035756, dated Jul. 31, 2019, 11 pages.

* cited by examiner

_US 10,780,217 B2_

RATCHET DRIVE FOR ON BODY DELIVERY SYSTEM

CROSS-REFERENCE TO RELATED APPLICATIONS

This application claims the benefit of U.S. Provisional Application No. 62/420,382, filed Nov. 10, 2016, and U.S. Provisional Application No. 62/439,822, filed Dec. 28, 2016, each of which is incorporated herein by reference in its entirety.

TECHNICAL FIELD

Embodiments generally relate to medication delivery. More particularly, embodiments relate to drive systems for drug delivery devices.

BACKGROUND

An on-body delivery system (OBDS) can be used to deliver drug dosages to a user over time. During a control system failure of the OBDS, there can be a risk of delivering too much of a drug to the user resulting in a possible drug overdose condition. Accordingly, there is a need for an OBDS having a drive system for delivering a drug to a user that can prevent delivery of too much of a drug to the user during a system failure.

DETAILED DESCRIPTION

This disclosure presents various systems, components, and methods related to a drug delivery device. Each of the systems, components, and methods disclosed herein provides one or more advantages over conventional systems, components, and methods.

Various embodiments provide for drug delivery using ratchet-based drive systems. The ratchet-based drive systems restrict angular movement and/or linear movement of components that cause a plunger to expel a liquid drug from a drug container. Movement of the components can be restricted to expel only a predetermined or desired amount of the liquid drug. In the case that control of the drive system is lost or fails, the maximum amount of drug that could be delivered is limited to a known amount, thereby reducing the likelihood of an overdose. The predetermined amount of the liquid drug expelled can correspond to any portion of the liquid drug including a single dose of the liquid drug or a portion thereof.

Figure 1:
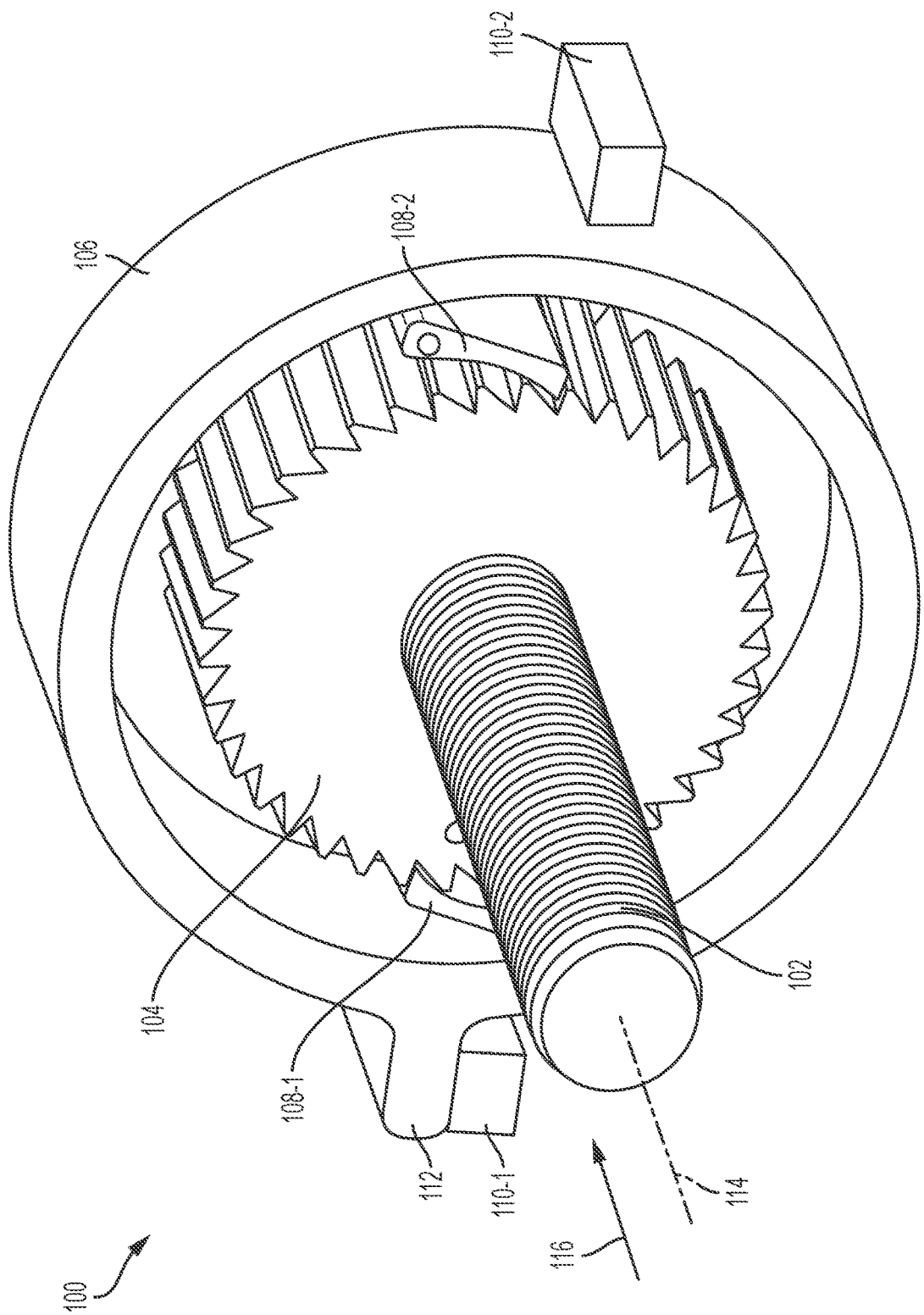
FIG. 1 illustrates a first exemplary ratchet drive system.

FIG. 1 illustrates a first exemplary ratchet drive system 100. The ratchet drive system 100 can be incorporated as part of an on-body delivery system (OBDS) as described herein. The ratchet drive system 100 can include a lead screw 102, a ratchet gear 104, a ratchet carrier 106, a first pawl 108-1, a second pawl 108-2, a first carrier stop 110-1, and a second carrier stop 110-2. As shown in FIG. 1, the lead screw 102 can be coupled to the ratchet gear 104 and can be positioned through the ratchet gear 104 (e.g., through a center hole of the ratchet gear 104). The lead screw 102 can include threads that engage the ratchet gear 104. The lead screw 102 can also be positioned through the ratchet carrier (e.g., through a center hole of the ratchet carrier 106). An end of the lead screw 102 that extends beyond the ratchet carrier 106 can be coupled to a plunger positioned within a drug cartridge (not shown in FIG. 1). The ratchet drive system 100 can be operated such that rotation of the lead screw 102 can cause the plunger to be advanced, thereby expelling a portion of a liquid drug stored in the drug cartridge. The ratchet drive system 100 can prevent over-delivery (e.g., overdose) of the liquid drug (e.g., during system failure of the OBDS incorporating the ratchet drive system 100) to ensure safe delivery of the liquid drug and operation of the OBDS as described herein.

The first and second pawls 108-1 and 108-2 can be coupled to the ratchet carrier 106. As shown in FIG. 1, the first and second pawls 108-1 and 108-2 can be positioned to engage the ratchet gear 104 (e.g., the outer teeth of the ratchet gear 104). To expel a portion of the liquid drug from the drug container, the ratchet carrier 104 can be rotated (e.g., about a central axis of rotation 114 in a clockwise direction with respect to the depiction of the ratchet drive system 100 in FIG. 1). The ratchet carrier 106 can be rotated by an amount corresponding to the position of the second carrier stop 110-2. That is, the ratchet carrier 106 can be rotated such that an extension or protrusion 112 of the ratchet carrier 106 moves from the first carrier stop 110-1 to the second carrier stop 110-2. The extension 112 of the ratchet carrier 106 can be stopped by or can be positioned adjacent to the second carrier stop 110-2 when a desired portion (e.g., a dose or portion thereof) of the liquid drug has been expelled from the drug container. The first and second carrier stops 110-1 and 110-2 can be coupled to a portion of the OBDS incorporating the ratchet drive system 100.

When the ratchet carrier 106 is rotated from the first carrier stop 110-1 toward the second carrier stop 110-2, the ratchet gear 104 can be caused to similarly rotate based on the engagement of the first and second pawls 108-1 and 108-2. That is, the first and second pawls 108-1 and 108-2 can couple the ratchet carrier 106 to the ratchet gear 104. The rotation of the ratchet gear 104 can cause the lead screw 102 to also rotate. The ratchet gear 104 can be tightly coupled to the lead screw 102 to ensure that rotation of the ratchet gear 104 results in rotation of the lead screw 102. Rotation of the lead screw 102 can cause the lead screw 102 to advance in a direction 116 that can be parallel to the central axis 114. This movement of the lead screw 102 can cause the plunger to move further into the drug container, which can cause a portion of the liquid drug stored therein to be expelled. The linear displacement of the lead screw 102 in the direction 116 caused by rotation of the ratchet carrier 106 and the ratchet gear 104 can be based on a thread pitch of the lead screw 102 which can be adjusted for particular applications and drug dosages. The amount of liquid drug expelled can correspond to a predetermined or desired amount of the liquid drug stored in the drug container. In various embodiments, any portion of the liquid drug can be expelled including, for example, a single dose of the liquid drug or a portion thereof. Accordingly, in various embodiments, movement of the ratchet carrier 106 from the first carrier stop 110-1 to the second carrier stop 110-2 can cause a single dose of the liquid drug to be expelled from the drug container for delivery to a patient or user.

After the ratchet carrier 106 has been moved to a position corresponding to the second carrier stop 110-2, the ratchet carrier 106 can be rotated back to a position corresponding to the first carrier stop 110-2 (e.g., as shown in FIG. 1). As shown in FIG. 1, the ratchet drive system 100 can be in an initial or reset state awaiting activation so as to rotate the ratchet carrier 106 toward the second carrier stop 110-2 for delivery of a portion of the liquid drug. Prior to rotating the ratchet carrier 106 back to a position corresponding the first carrier stop 110-1 as shown in FIG. 1, the first and second pawls 108-1 and 108-2 can be disengaged from the ratchet gear 104. Releasing the first and second pawls 108-1 and 108-2 from the ratchet gear 104 can prevent the ratchet gear 104 from rotating when the ratchet carrier 106 is rotated back toward the first carrier stop 110-1. As a result, the position of the lead screw 102 is maintained (e.g., the lead screw 102 is not advanced in the direction 116 when the ratchet carrier 106 is rotated back toward the first carrier stop 110-1). The first and second pawls 108-1 and 108-2 can then re-engage the ratchet gear 104 after the ratchet carrier 104 is moved back to the position shown in FIG. 1. The ratchet drive system 100 can then await a subsequent activation (e.g., an instruction to rotate the ratchet carrier 106 toward the second carrier stop 110-2) for a next cycle of drug delivery. The first and second pawls 108-1 and 108-2 can be coupled to a control system that can rotate or otherwise adjust the position of the first and second pawls 108-1 and 108-2 to engage and disengage the ratchet gear 104 as desired.

In various embodiments, the ratchet carrier 106 can be positioned around the ratchet gear 104. The ratchet gear 104 can be positioned within an opening of the ratchet carrier 106. In various embodiments, the ratchet drive system 100 can include a single pawl or more than two pawls.

The operation of the ratchet drive system 100 can prevent over-delivery of the liquid drug that the ratchet drive system 100 can be used to expel from the drug container. The second carrier stop 110-2 can prevent the lead screw 102 from rotating more than a desired amount, by restricting further rotation of the ratchet carrier 106, thereby restricting further advancement of the plunger coupled to the lead screw 102. As a result, further delivery of the liquid drug is prevented. During system failure of the OBDS that incorporates the ratchet drive system 100 (e.g., a power failure), the risk of over-delivery of the liquid drug is mitigated by the restricted movement of the lead screw 102. Precise dosing of the liquid drug can also be provided by the ratchet drive system 100.

The first and second carrier stops 110-1 and 110-2 can be displaced by any amount. As shown in FIG. 1, the first and second carrier stops 110-1 and 110-2 are displaced by approximately 180 degrees but are not so limited. The displacement of the first and second carrier stops 110-1 and 110-2 can correspond to delivery of a predetermined or desired amount of the liquid drug when the ratchet carrier 106 is rotated from the first carrier stop 110-1 to the second carrier stop 110-2 but is not so limited. In various embodiments, the predetermined amount of the liquid drug can correspond to a single dose of the liquid drug or a portion thereof.

The ratchet carrier 106 can be coupled to a power source to effectuate rotation of the ratchet carrier 106. The power source can comprise a motor but is not so limited. The power source can comprise a mechanical system or an electromechanical system. The power source can cause the ratchet carrier 106 to be rotated toward the second carrier stop 110-1 based upon an activation signal provided by the OBDS (e.g., a controller). The activation can be automatically provided or can be generated responsive to a user input. The power source can cause the ratchet carrier 106 to rotate back toward the first carrier stop 110-1 immediately after providing the dosage of the liquid drug or after a predetermined delay.

The OBDS in which the ratchet drive system 100 can be incorporated can be any type of wearable drug delivery system such as, for example, the OmniPod® (Insulet Corporation, Billerica, Mass.) insulin delivery device and/or a drug delivery device such as those described in U.S. Pat. Nos. 7,303,549, 7,137,964, or U.S. Pat. No. 6,740,059, each of which is incorporated herein by reference in its entirety.

Figure 2:
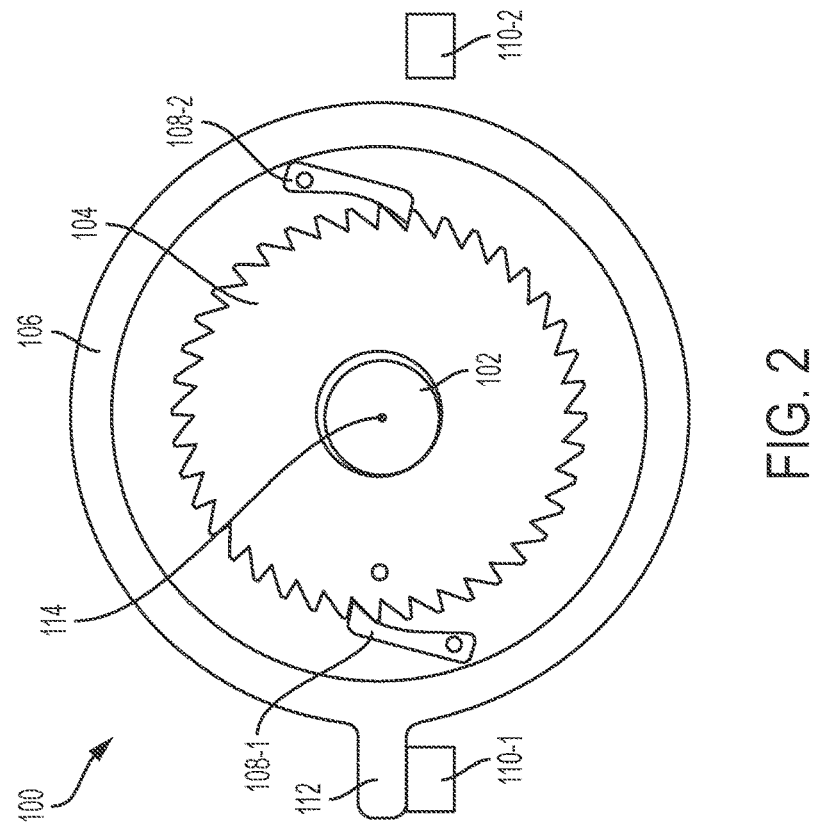
FIG. 2 illustrates the first ratchet drive system in an idle state.

FIG. 2 illustrates a second view of the ratchet drive system 100 depicted in FIG. 1. FIG. 1 can represent an isometric view of the ratchet drive system 100. FIG. 2 can represent a corresponding front view of the ratchet drive system 100. As shown in FIG. 2, the extension 112 can be positioned adjacent to the first carrier stop 110-1 and the first and second pawls 108-1 and 108-2 can be engaged with the ratchet gear 104. FIG. 2 can represent the ratchet drive system 100 in an initial or idle state prior to being activated to rotate the ratchet carrier 106. Further, the ratchet carrier 106 can be considered to be in an initial position as depicted in FIG. 2.

Figure 3:
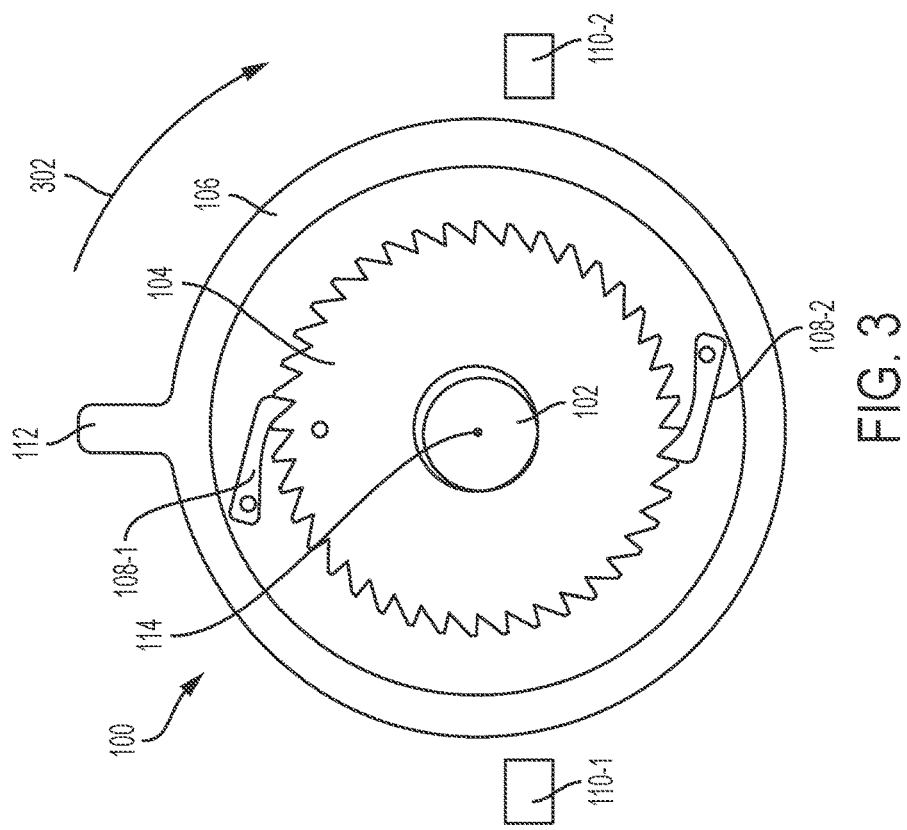
FIG. 3 illustrates the first ratchet drive system during delivery of a drug.

FIG. 3 illustrates a front view of the ratchet drive system 100 during delivery of the liquid drug. As shown in FIG. 3, the ratchet carrier 106 is rotated in a direction 302 (e.g., a clockwise direction relative to the depiction of the ratchet drive system 100 in FIG. 3). As shown, the extension 112 is moving toward the second carrier stop 110-2. The first and second pawls 108-1 and 108-2, the ratchet gear 104, and the lead screw 102 each correspondingly rotate in the direction 302. Further, the lead screw 102 is linearly displaced in a direction parallel to the central axis 114.

Figure 4:
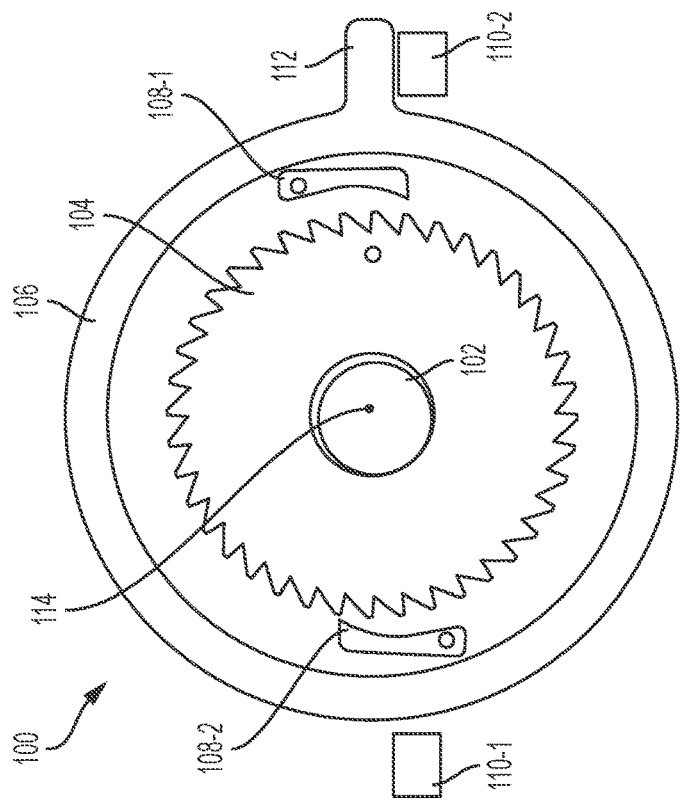
FIG. 4 illustrates the first ratchet drive system after delivery of the drug.

FIG. 4 illustrates a front view of the ratchet drive system 100 after delivery of the liquid drug. As shown in FIG. 4, the ratchet carrier 106 has been rotated such that the extension 112 is positioned adjacent to the second carrier stop 110-2.

The second carrier stop 110-2 can prevent the ratchet carrier 106 from rotating any further, thereby preventing further linear displacement of the lead screw 102. The rotation of the ratchet carrier 106 from the first carrier stop 110-1 to the second carrier stop 110-2 can correspond to expelling and delivering a desired amount or portion of the liquid drug. The ratchet carrier 106 can be considered to be in a final position as depicted in FIG. 4.

Figure 5:
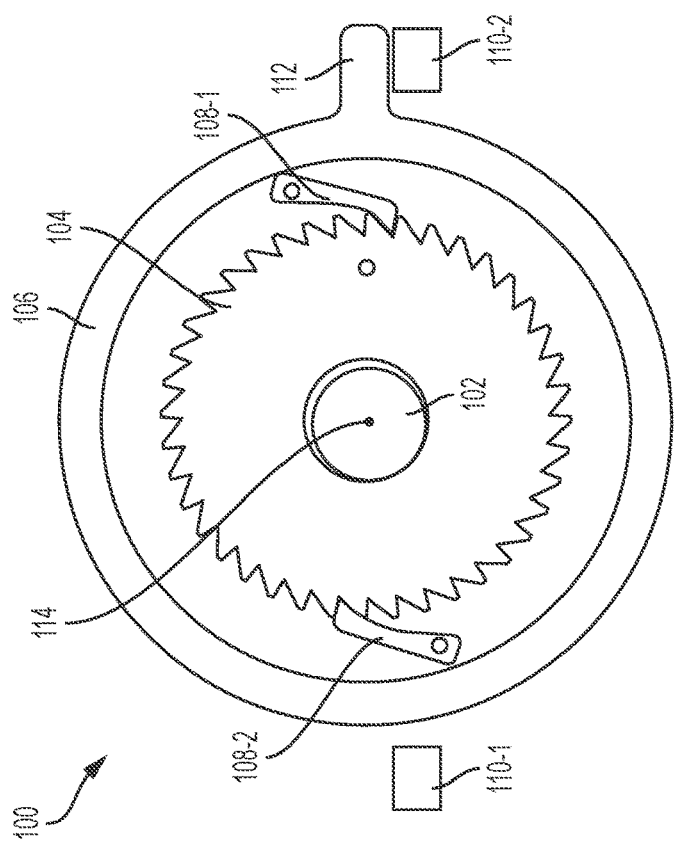
FIG. 5 illustrates the first ratchet drive system during a first phase of reset.

FIG. 5 illustrates a front view of the ratchet drive system 100 during an initial resetting of the ratchet drive system 100. As shown in FIG. 5, the first and second pawls 108-1 and 108-2 are disengaged from the ratchet gear 104. Accordingly, when the ratchet carrier 106 is rotated back toward the first carrier stop 110-1, the ratchet gear 104 and the lead screw 102 will remain stationary. As a result, none of the liquid drug will be expelled from the drug container when the ratchet carrier 106 is rotated back towards the first carrier stop 110-1.

Figure 6:
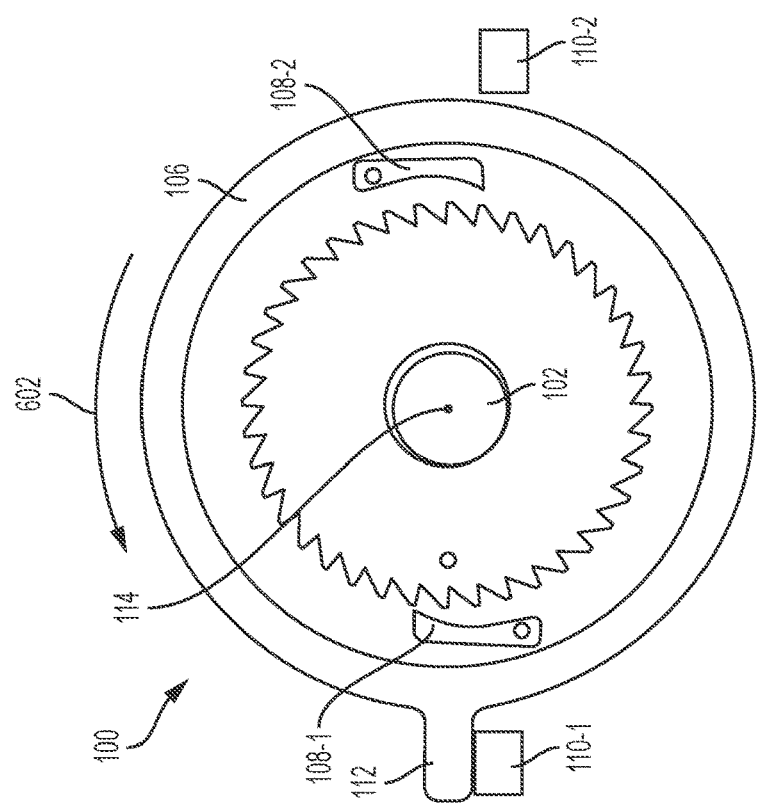
FIG. 6 illustrates the first ratchet drive system during a second phase of reset.

FIG. 6 illustrates a front view of the ratchet drive system 100 during further resetting of the ratchet drive system 100. As shown in FIG. 6, the ratchet carrier 106 is rotated in a direction 602 (e.g., a counter-clockwise direction relative to the depiction of the ratchet drive system 100 in FIG. 6). As shown, the extension 112 is moved toward the first carrier stop 110-1 and is shown positioned adjacent to the first carrier stop 110-1 (e.g., corresponding to the initial position of the ratchet carrier 106). The first and second pawls 108-1 and 108-2 are similarly rotated in the direction 602. After the ratchet carrier 106 is fully rotated back to the initial position (e.g., to a reset or the initial position), the first and second pawls 108-1 and 108-2 can re-engage the ratchet gear 104 (e.g., as depicted in FIG. 2). The ratchet drive system 100 can then remain in the reset or idle state until being activated again to repeat delivery and the reset cycle as described herein. As with the second carrier stop 110-2, the first carrier stop 110-1 can also restrict further rotation of the ratchet carrier 106.

Figure 7:
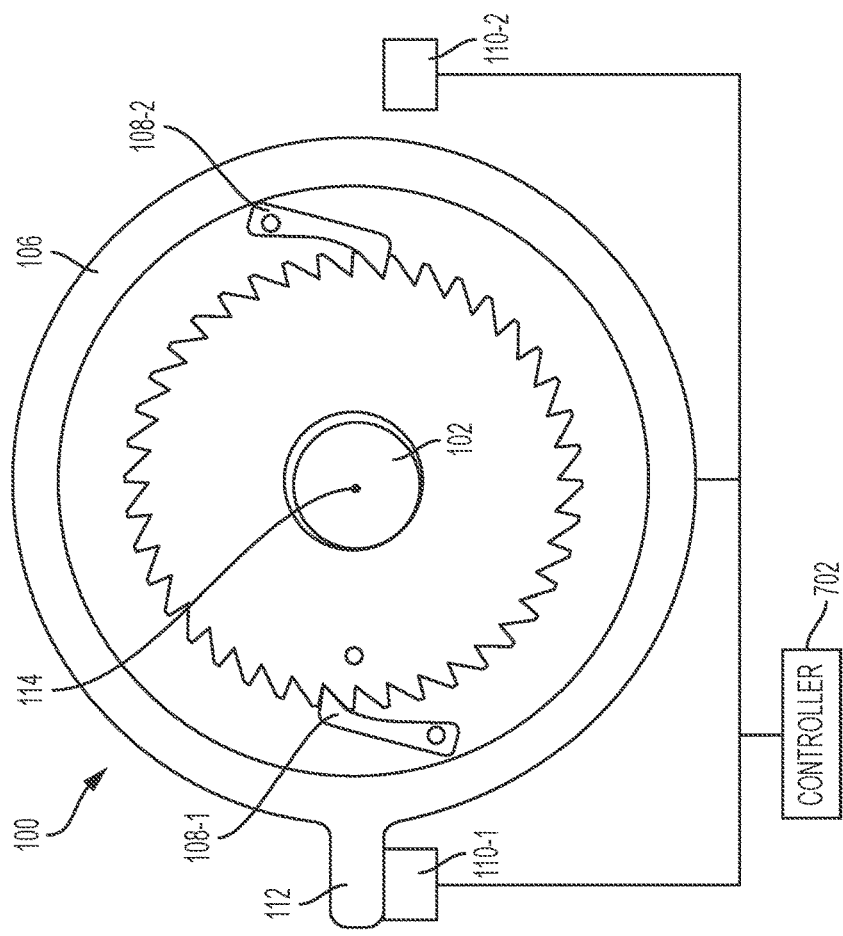
FIG. 7 illustrates the first ratchet drive system in relation to a controller.

FIG. 7 illustrates the ratchet drive system 100 with an exemplary controller 702. The controller 702 can be coupled to the first carrier stop 110-1, the second carrier stop 110-1, and any other component of the ratchet drive system 100 such as the ratchet carrier 106. The controller 702 can direct operation of the ratchet drive system 100. The first and second carrier stops 110-1 and 110-2 can each include one or more sensors that can inform the controller 702 as to the position of the ratchet carrier 106. For example, the first and second carrier stops 110-1 and 110-2 can each include a sensor that can inform the controller 702 when the extension 112 is touching or in close proximity to one of the first and second carrier stops 110-1 and 110-2. Positional information of the ratchet carrier 106 can also be provided to the controller 702 from rotation of the ratchet carrier 106. The controller 702 can be coupled to the power source of the ratchet drive system 100 to direct the power source to rotate the ratchet carrier 106 in a desired direction based on, for example, positional information of the ratchet carrier 106 provided by at least the first and second carrier stops 110-1 and 110-2.

During delivery of a portion of the liquid drug, the sensor in the second carrier stop 110-2 can send a signal to the controller 702 indicating the position of the extension 112 (e.g., when the extension touches or is adjacent to the second carrier stop 110-2). The controller 702 can adjust or stop the rotation of the ratchet carrier 106 (e.g., in the direction 302) based on signals received from the second carrier stop 110-2. Further, signals from the second carrier stop 110-2 can allow the controller 702 to maintain a count of the number times the extension 112 has reached the second carrier stop 110-2. In this way, a count of the number of times the drug is delivered or expelled can be maintained, along with a count of the remaining number of times the drug can be expelled. In various embodiments, when the portion expelled corresponds to a desired dose of the liquid drug or portion thereof, a count of the number of doses of drug delivered or expelled can be maintained, along with a count of remaining doses.

The sensor in the first carrier stop 110-1 can similarly send a signal to the controller 702 indicating the position of the extension 112 (e.g., when the extension touches or is adjacent to the first carrier stop 110-1). The controller 702 can adjust or stop the rotation of the ratchet carrier 106 (e.g., in the direction 602) based on signals received from the first carrier stop 110-1. Signals from the first carrier stop 110-1 can also be used to maintain a count of the number of times the liquid drug is delivered or expelled and a count of how many more times the drug can be expelled before the drug container is substantially empty. As described above, in various embodiments, when the portion expelled corresponds to a desired dose of the liquid drug or portion thereof, the signals from the first carrier stop 110-1 can enable a count of the number of doses of drug delivered or expelled can be maintained, along with a count of remaining doses.

Figure 8:
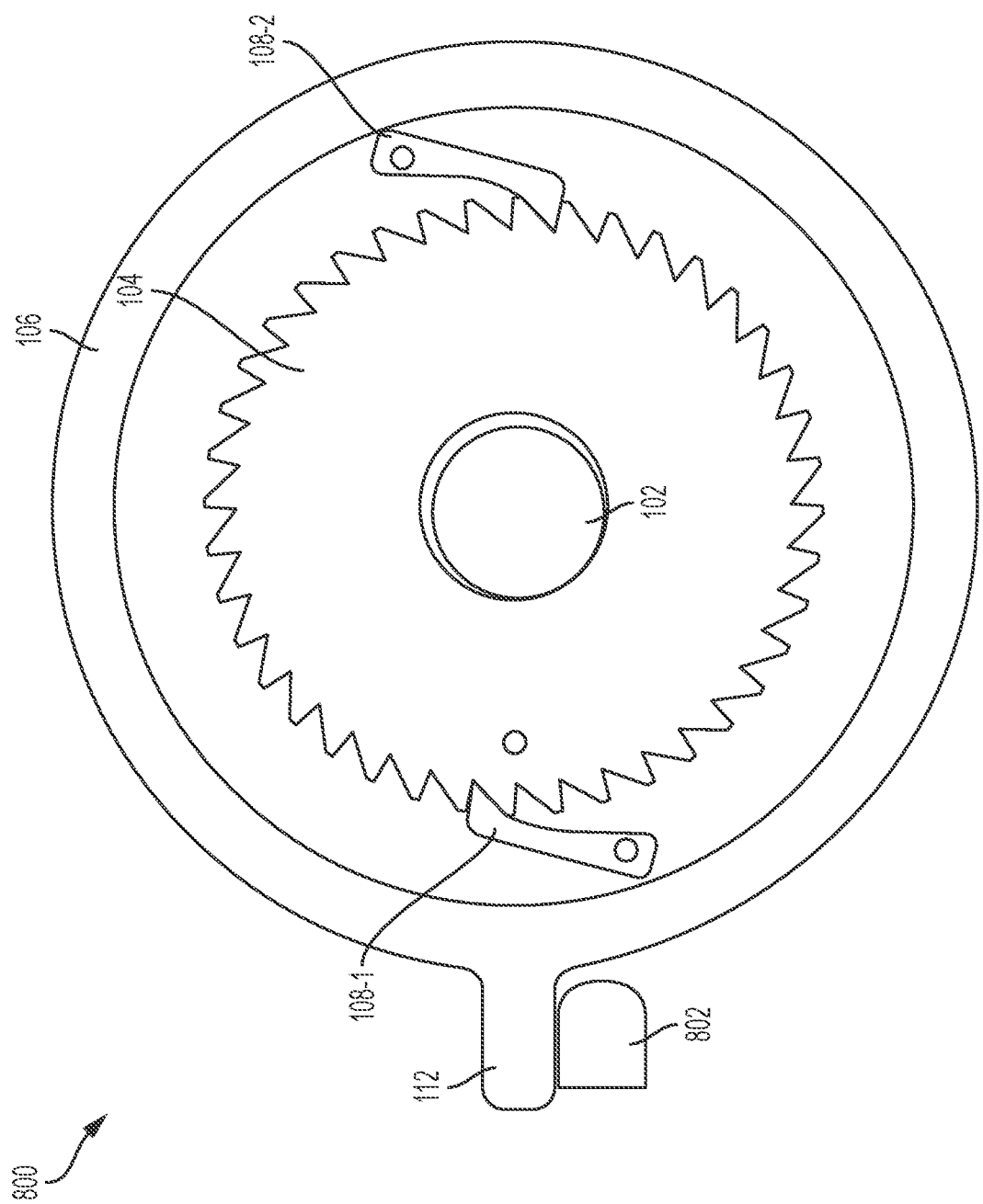
FIG. 8 illustrates a second exemplary ratchet drive system.

FIG. 8 illustrates a second exemplary ratchet drive system 800. The ratchet drive system 800 can include substantially the same components of the ratchet drive system 100 and can operate in a substantially similar manner as the ratchet drive system 100. The ratchet drive system 800 can include a single carrier stop 802 (as opposed to two carrier stops as included with the ratchet drive system 100). The ratchet drive system 800 as shown in FIG. 8 can be in an initial position or idle state prior to being activated to deliver a portion of the liquid drug. When activated or instructed to deliver a portion of the liquid drug, the ratchet carrier 106 can rotate in a clockwise direction (relative to the depiction of the ratchet drive system 800 in FIG. 8). The extension 112 can rotate until reaching the other side of the carrier stop 802. In doing so, the ratchet gear 104 and the lead screw 102 can similarly rotate. A desired amount of drug can be expelled from the drug container based on this rotation of the ratchet carrier 106.

The carrier stop 802 can include one or more sensors for detecting a position of the ratchet carrier 106. As with the ratchet drive system 100, the ratchet drive system 800 can further include a controller for directing operation of the ratchet drive system 800 based on signals received from one or more sensors of the carrier stop 802. Like the ratchet drive system 100, the ratchet drive system 800 can be coupled to a power source (e.g., a motor) to provide an input for rotating the ratchet carrier 106.

Figure 9:
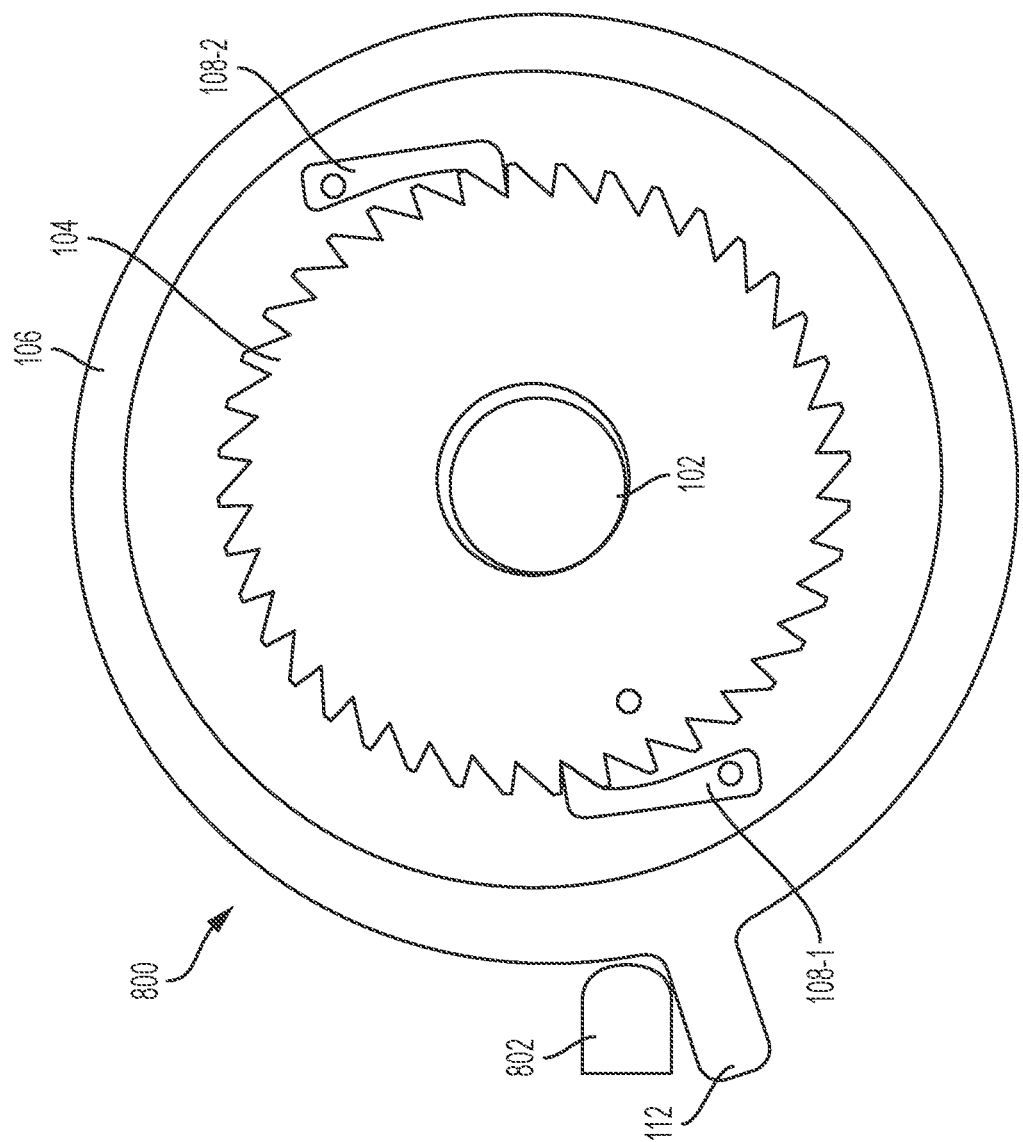
FIG. 9 illustrates the second ratchet drive system after delivery of a drug.

FIG. 9 illustrates the ratchet drive system 800 after delivering a portion of the liquid drug. As shown in FIG. 9, the ratchet carrier 106 has rotated such that the extension 112 is positioned on the other side of the carrier stop 802 (as compared to the position of the extension 112 as shown in FIG. 8). The first and second pawls 108-1 and 108-2 and the ratchet gear 104 have similarly rotated. The ratchet carrier 106 has rotated just under 360 degrees. For a motor power source, the implementation of the ratchet drive system 800 with the single carrier stop 802 can reduce the number of motor cycles used to deliver the same advancement of the lead screw 102.

Figure 10:
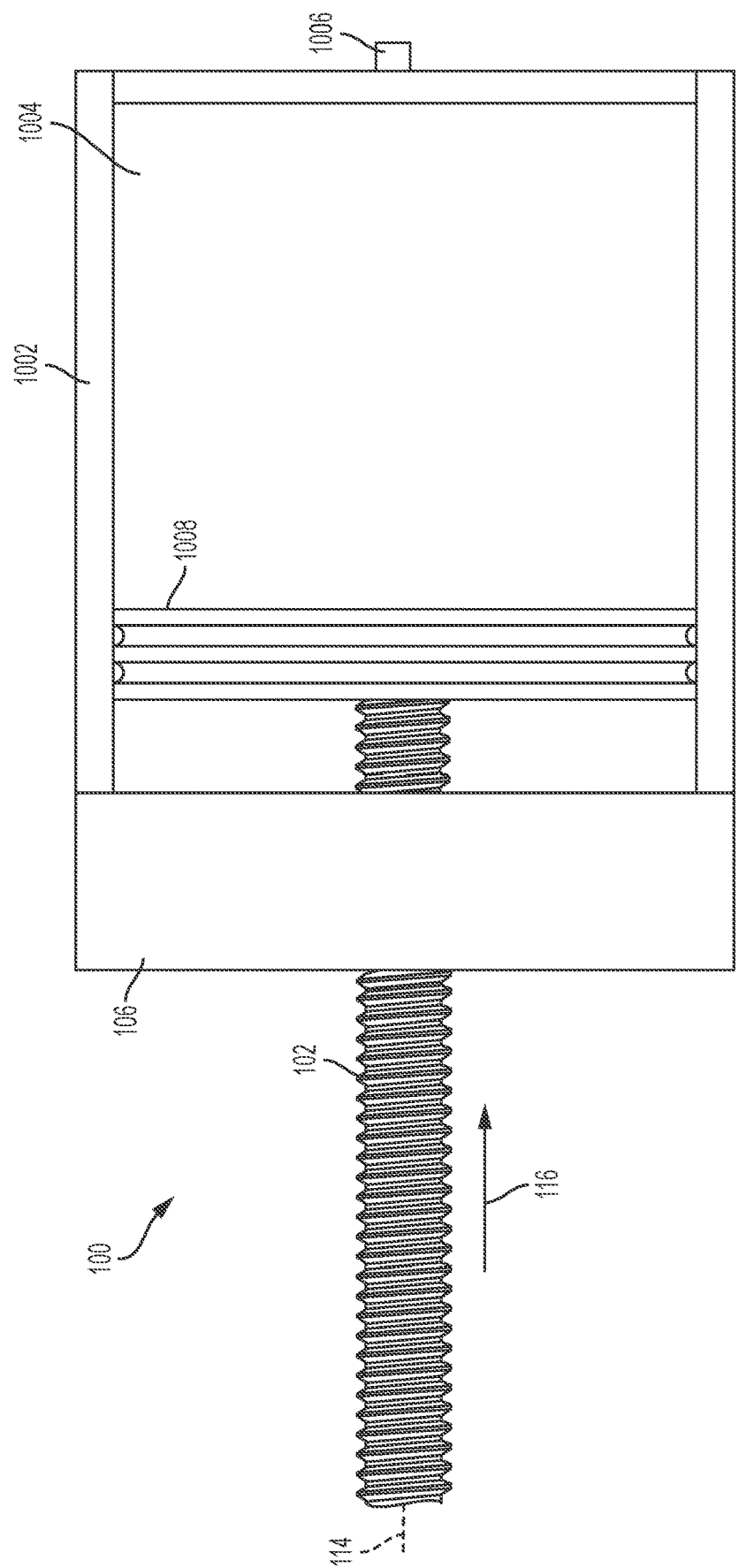
FIG. 10 illustrates the first ratchet drive system in relation to a drug container.

FIG. 10 illustrates a side view of the ratchet drive system 100 in relationship to a drug container 1002. For simplicity, the first and second carrier stops 110-2 and 110-2 are not shown. As shown in FIG. 10, the lead screw 102 extends through and beyond the ratchet carrier 106 (e.g., through a central hole or opening of the ratchet carrier 106). The ratchet carrier 106 can be coupled to or positioned adjacent to the drug container 1002. The drug container 1002 can include an area or reservoir 1004 for holding a liquid drug as described herein. The drug container 1002 can further include a port 1006 through which the liquid drug stored in the reservoir 1004 can be expelled out of the drug container 1002.

The lead screw 102 can be coupled to a plunger 1008. The plunger 1008 can define a boundary of the reservoir 1004. As described herein, when the ratchet carrier 106 is rotated in a first direction to initiate drug delivery, the lead screw 102 can rotate about the central axis 114. As a result, the lead screw 102 can move in the direction 116 and can push on the plunger 1008 to drive the plunger 1008 in the direction 116 as well. The movement of the plunger 1008 in the direction 116 can expel a portion of the liquid drug stored in the reservoir 1004 from the drug container 1002 (e.g., through the exit port 1006 for subsequent delivery to a patient).

The ratchet drive system 100 and additional components depicted in FIG. 10 can be incorporated into an OBDS as described herein. The ratchet drive system 800 can be similarly coupled to the additional components depicted in FIG. 10 as will be understood by a person of ordinary skill in the art. As described herein, the ratchet drive systems 100 and 800 can prevent overdose situations that can occur with conventional drive systems for drug delivery devices by restricting rotational movement and using multiple rotational cycles to deliver one or more desired or predetermined doses of the liquid drug.

For example, if the power source for the ratchet drive system 100 suddenly and/or catastrophically failed at any time (e.g., during delivery of a dose and/or movement of ratchet carrier 106 toward the second carrier stop 110-2), then the second carrier stop 110-2 can restrict the angular movement of the ratchet carrier 106. As a result, delivery of any further drug can be prevented. In particular, the second carrier stop 110-2 can block movement of the ratchet carrier 106 that could be caused by any force such as inertia or gravity that may attempt to rotate the ratchet carrier 106 any further. As described herein, the maximum angular movement of the ratchet carrier 106 can be restricted by a desired amount such that the angular displacement corresponds to a desired drug delivery, ensuring that drug delivery can be limited to a desired amount in a runaway operation condition. In various embodiments, as described above in relation to the other disclosed ratchet drive systems, any portion of the stored liquid drug can be delivered during each cycle of movement including, for example, a single desired dose of the liquid drug or a portion thereof. The ratchet drive system 800 provides the same prevention of overdose during such conditions by the carrier stop 802 similarly restricting movement of the ratchet carrier 106.

Figure 19:
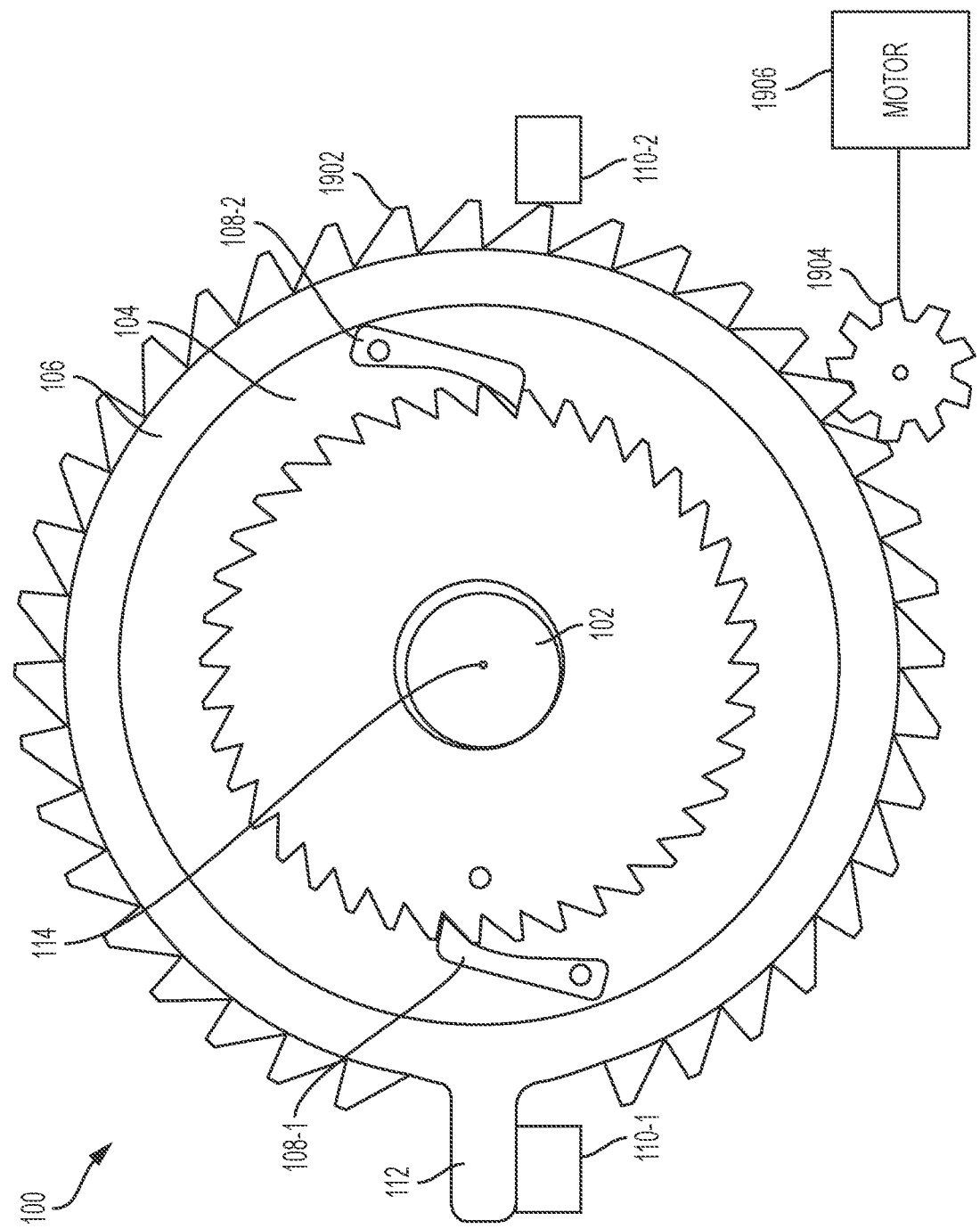
FIG. 19 illustrates the first ratchet drive system in relation to a power source.

FIG. 19 illustrates the ratchet drive system 100 with an exemplary power source 1906. The power source 1906 can be a motor. The motor 1906 can interface with the ratchet drive system 100 as shown to facilitate movement of the ratchet carrier 106 as described herein.

In various embodiments, as shown in FIG. 19, the ratchet carrier 106 can include gear teeth 1902. The gear teeth 1902 can be positioned along a perimeter of the ratchet carrier 106 and can project from the ratchet carrier 106. A gear 1904 can be coupled to the ratchet carrier 106 as shown. In various embodiments, teeth of the gear 1904 can interface with the gear teeth 1902 of the ratchet carrier 106. The gear 1904 can be coupled to the motor 1906. The motor 1906 can rotate the ratchet gear 1906 as desired and as described herein by rotation of the gear 1904 as will be understood by a person of ordinary skill in the art. Accordingly, the motor 1906 can control delivery of the liquid drug by rotating the ratchet carrier 106 as desired and can rotate the ratchet carrier 106 back to an idle state after delivery. The motor 1906 can initiate rotation automatically or based on user input.

In various embodiments, the ratchet drive systems 100 and 800 can be configured to enable a portion of the drug to be delivered based on both forward and backwards rotation of the ratchet carrier 106 as will be appreciated by one skilled in the art.

Figure 11:
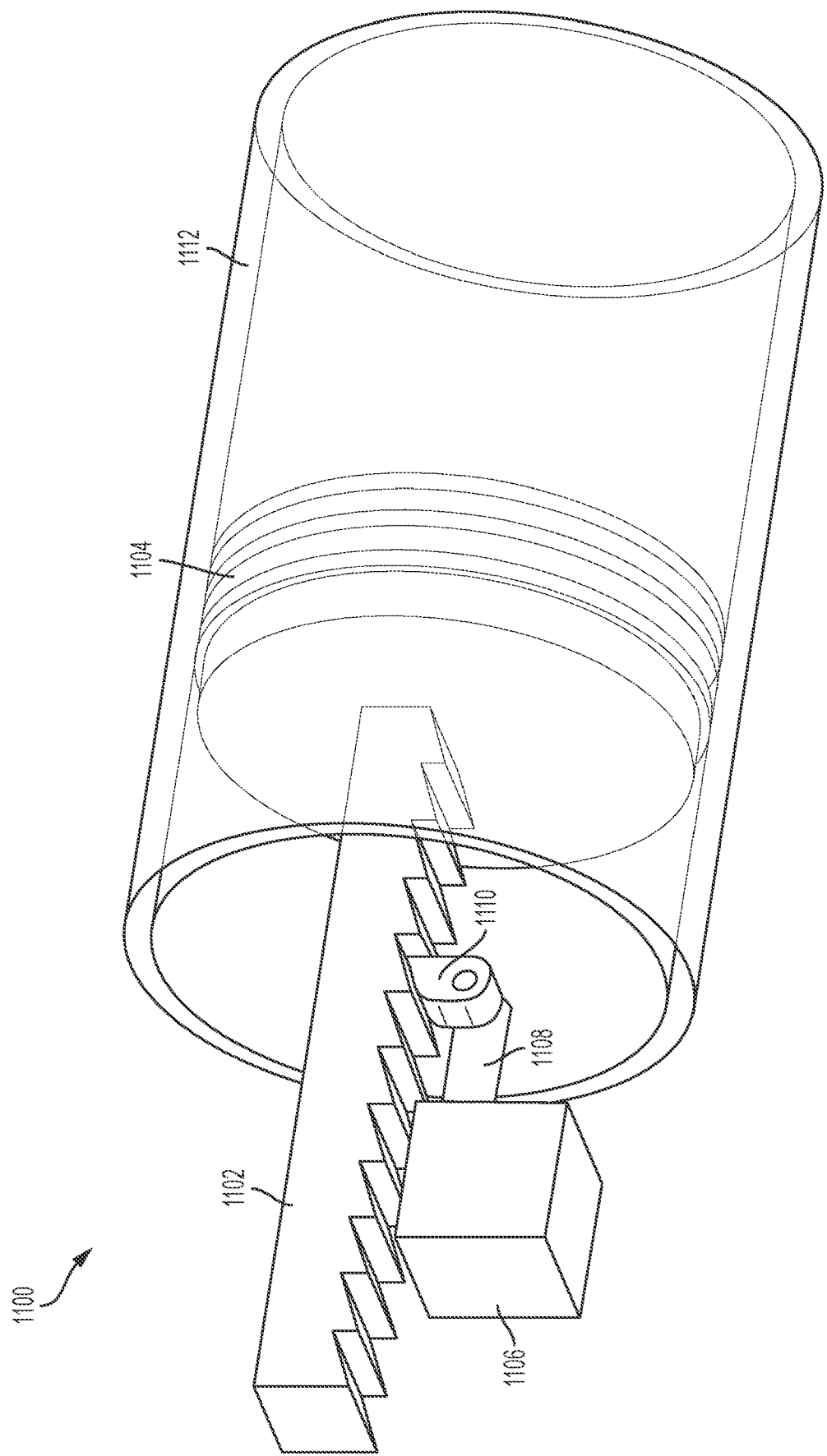
FIG. 11 illustrates a third exemplary ratchet drive system.

FIG. 11 illustrates a third exemplary ratchet drive system 1100. As with the ratchet drive systems 100 and 800, the ratchet drive system 1100 can be used in an OBDS as described herein. The ratchet drive system 1100 can include a rack 1102, a plunger 1104, a power source 1106, an arm 1108, a pawl 1110, and a drug container 1112. As shown in FIG. 11, the rack 1102 can be coupled to the plunger 1104. The plunger 1104 can be positioned within the drug container 1112. The power source 1106 can be, for example, a motor or a linear actuator. The power source 1106 can be coupled to the arm 1108. The pawl 1110 can be coupled to the arm 1108.

The ratchet drive system 1100 can be operated such that linear movement of the arm 1108 (e.g., in a direction away from the power source 1106) can drive the plunger 1104 further into the drug container 1112, thereby expelling a portion of a liquid drug stored in the drug cartridge. Like the ratchet drive systems 100 and 800, the ratchet drive system 1100 can prevent over-delivery (e.g., overdose) of the liquid drug (e.g., during system failure of the OBDS incorporating the ratchet drive system 1100) to ensure safe delivery of the liquid drug and operation of the OBDS as described herein.

FIG. 11 can represent the ratchet drive system 1100 in an idle state prior to activation. When activated, the ratchet drive system 1100 can operate to deliver a desired amount of the stored liquid drug to a user. Specifically, when activated, the power source 1106 can cause the arm 1108 to extend (e.g., in a direction away from the power source 1106). When the arm 1108 extends, the rack 1102 can be caused to move forward (e.g., in the same direction that the arm 108 extends) by the coupling of the arm 1108 to the rack 1102 by the pawl 1110. As a result, the plunger 1104 is driven further into the drug container, expelling a portion of the stored liquid drug.

The arm 1108 can be sized and controlled to extend a desired amount away from the power source 1106 when the ratchet drive system 1100 is activated. By limiting the amount by which the arm 1108 can extend (e.g., to a maximum extension amount), the movement of the plunger 1104 can likewise be limited. In this way, over-delivery can be mitigated by limiting the amount of liquid drug that can be expelled during each activation of the ratchet drive system 1100. After the arm 1108 is fully extended, the arm 1108 can be operated to move back to its original position (e.g., retracted back toward the power source 1106). The position of the rack 1102 can be maintained by having the pawl 1110 disengage the rack 1102 prior to the arm 1108 moving in a direction back toward the power source 1108.

The ratchet drive system 1100 can be used with the same OBDSs described in relation to the ratchet drive systems 100 and 800. Like the ratchet drive systems 100 and 800, a controller can be used with the ratchet drive system 1100 to direct operation of the power source 1106 and therefore delivery of the liquid drug. The controller can direct operation of the power source 1106 based on, for example, positional information of the plunger 1104, the rack 1102, and/or the arm 1108. The controller can track delivery of the liquid drug to determine a number of times a portion of the drug is delivered and/or an amount of liquid drug remaining as described herein, for example based on the movement of the arm 1108. The drug container 1112, like the drug container 1002, can include a port for the liquid drug (not shown in FIG. 11).

Figure 12:
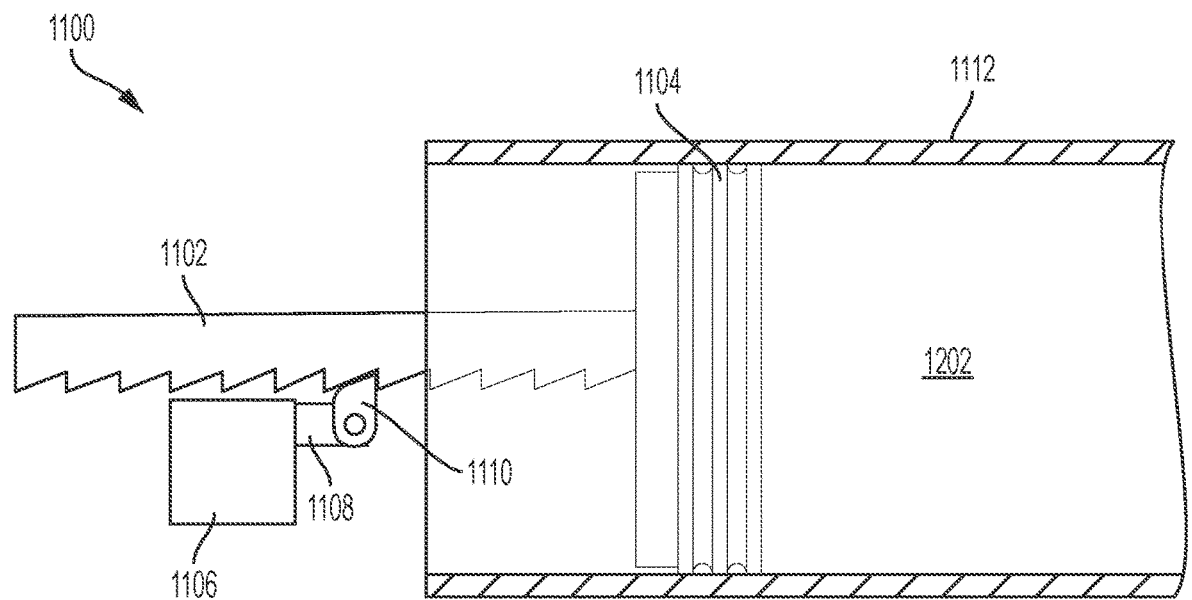
FIG. 12 illustrates the third ratchet drive system in an idle state.

FIG. 12 illustrates a second view of the ratchet drive system 1100 depicted in FIG. 11. FIG. 11 can represent an isometric view of the ratchet drive system 1100. FIG. 12 can represent a corresponding side view of the ratchet drive system 1100. As shown in FIG. 12, the pawl 1110 couples the arm 1108 to the rack 1102. The drug container 1112 includes a reservoir 1202 for storing the liquid drug. The reservoir 1202 can be defined in part by the plunger 1104 and an end of the drug container (opposite to the plunger 1104; not shown in FIG. 12). The end of the drug container 1112 can include a port or other opening allowing the liquid drug stored in the reservoir 1202 to be expelled as the plunger 1104 is advanced toward the end of the drug container 1112.

Figure 13:
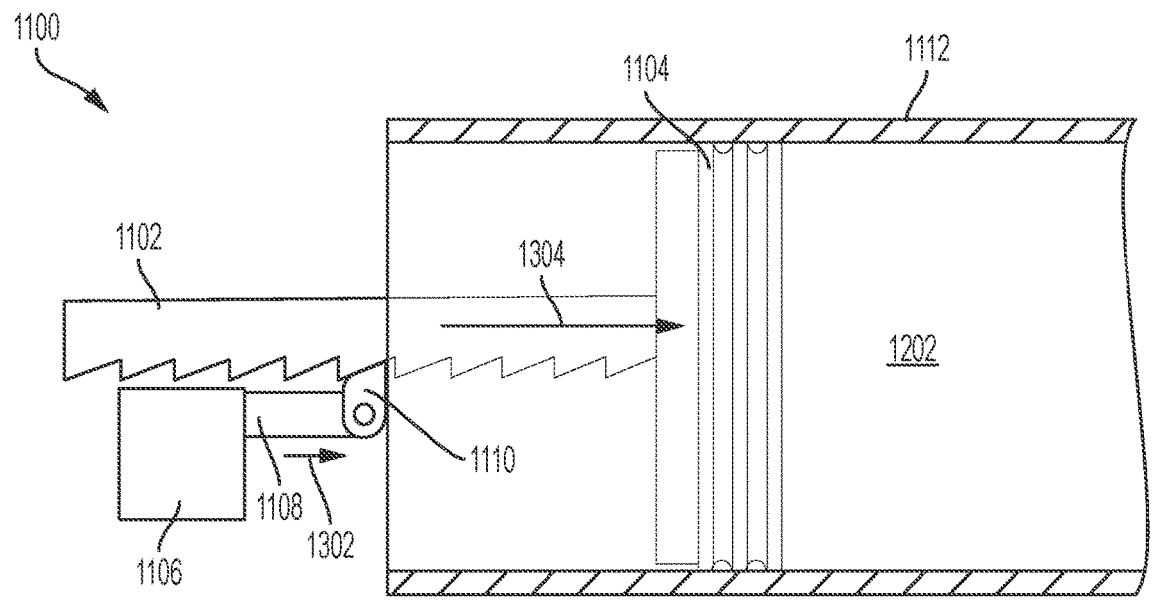
FIG. 13 illustrates the third ratchet drive system during delivery of a drug.

FIG. 13 illustrates the ratchet drive system 1100 during delivery of the liquid drug. As shown in FIG. 13, the arm 1108 extends in a direction 1302. As a result, the rack 1102 and plunger 1104 are advanced in a direction 1304 as shown. The advancement of the plunger 1104 further into the drug container 1112 can cause a portion of the liquid drug stored in the reservoir 1202 to be expelled from the drug container 1112. The arm 1108 can be sized such that extension of the arm 1108 in the direction 1302 corresponds to a desired amount of the liquid drug being expelled (e.g., a single dose or a portion thereof). As described herein, the length of the arm 1108 can be limited such that only a desired amount of the liquid drug is expelled by moving the rack 1102 and the plunger 1104 by the amount the arm 1108 is extended. Runaway operation and over-delivery of the liquid drug can therefore be avoided in case of a system failure (e.g., power loss) of the OBDS in which the ratchet drive system 1100 is incorporated since further movement of the rack 1102 by the arm 1108 is restricted.

After the arm 1108 is extended by the set amount, the arm 1108 and the rack 1102 can come to a rest. The controller can track the movement of the arm 1008 and can maintain a count of the number of times the arm 1108 is extended to expel the liquid drug. The amount the arm 1108 is extended can correspond to any desired amount of drug to be delivered to a user including, for example, a single dose of the liquid drug, or a portion thereof.

Figure 14:
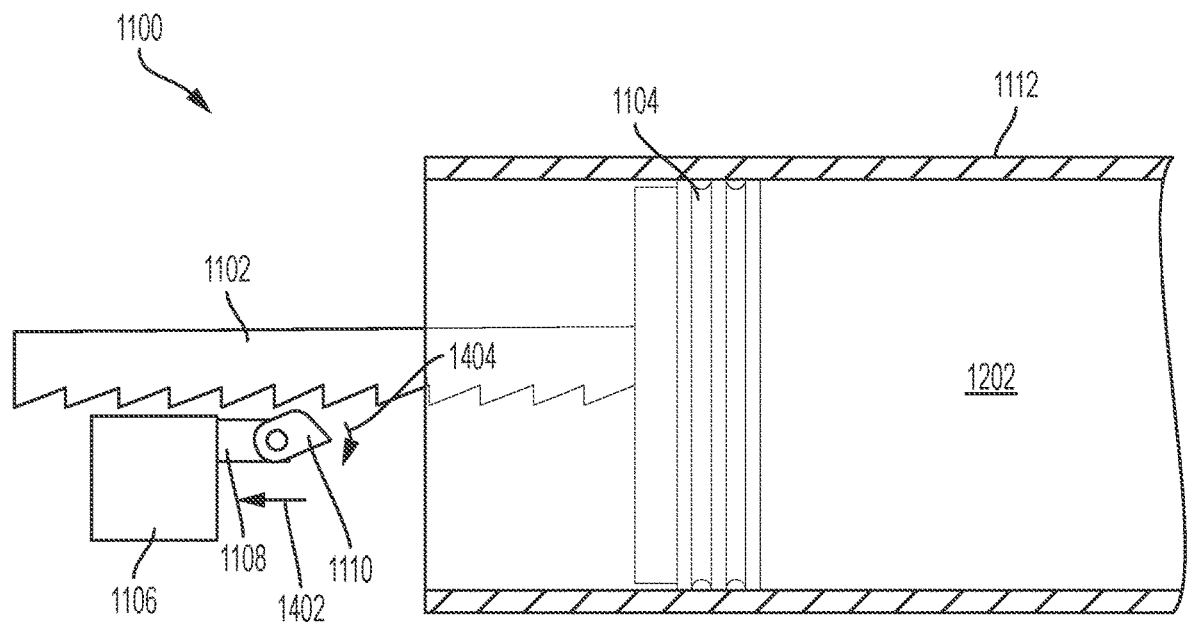
FIG. 14 illustrates the third ratchet drive system after delivery of the drug during a first phase of reset.

FIG. 14 illustrates the ratchet drive system 1100 initiating a return to its initial or idle state. As shown in FIG. 14, the arm 1108 is a moved in a direction 1402 back toward the power source 1106. The pawl 1110 is shaped so as to rotate in a direction 1404 as the arm 1108 is moved in the direction 1402. As a result, the pawl 1110 is disengaged from the rack 1102. The rack 1102 therefore does not move and remains stationary as the arm 1108 is moved backwards (e.g., in the direction 1402). In various embodiments, the pawl 1110 can be controlled to rotate in the direction 1404 to facilitate disengagement from the rack 1102. The arm 1108 can be retracted back to an original position corresponding to the position of the arm 1108 prior to activation.

Figure 15:
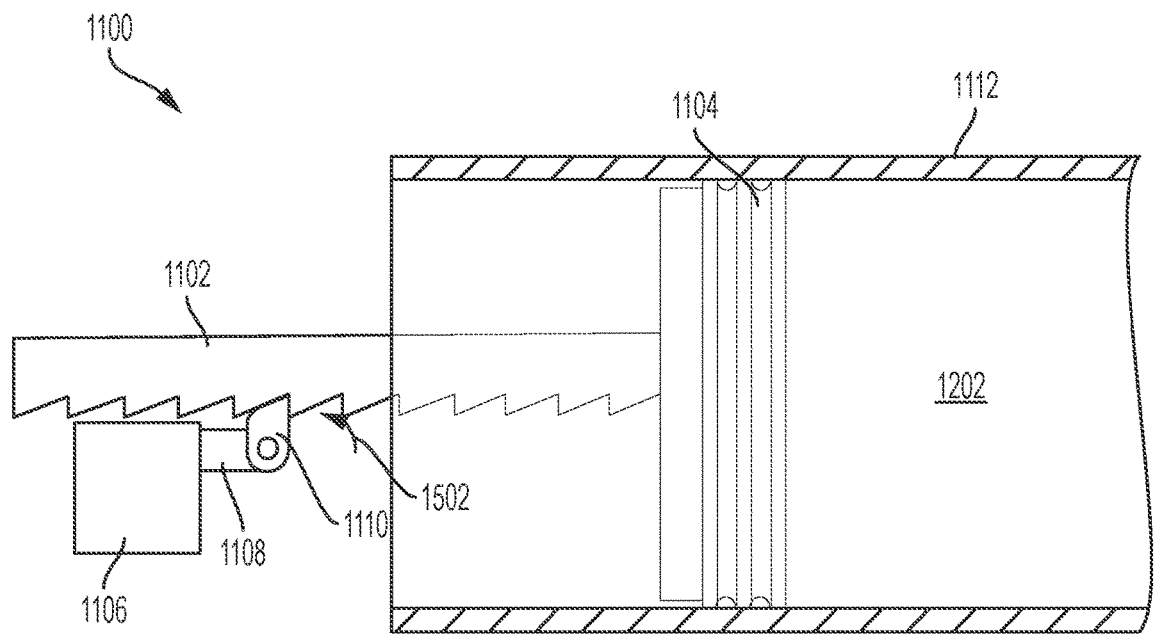
FIG. 15 illustrates the third ratchet drive system during a second phase of reset.

FIG. 15 illustrates the ratchet drive system 1100 re-engaging the rack 1102. As shown in FIG. 15, the arm 1108 is in close proximity to the power source 1106. When the arm 1108 stops moving, the pawl 1110 rotates in a direction 1502 to re-engage the rack 1102. Once the pawl 1110 re-engages the rack 1102, the ratchet drive system 1110 can be re-activated to a deliver a subsequent amount of the liquid drug.

In various embodiments, the stroke of the arm 1108 can be greater than a length of one tooth on of the rack 1102 so as to provide clearance for the pawl 1110 to rotate as described herein without hitting a tooth of the rack 1102. In various embodiments, the rotational movement of the pawl 1110 and/or the linear movement of the pawl 1110 can be passive movements, as the angle of the rack 1102 can push the pawl 1110 out of the way. In such embodiments, the pawl 1110 can be spring loaded, for example, and biased to be in the engaged position as shown in FIG. 15. As described above, in various other embodiments, the pawl 1110 can be actively rotated as desired for retraction, using a separate power source for example.

As described herein, the ratchet drive system 1100 can also prevent overdose situations that can occur with conventional drive systems for drug delivery devices by restricting linear movement and using multiple actuations cycles to deliver one or more doses of the liquid drug. For example, if the power source 1108 suddenly and/or catastrophically fails at any time (e.g., during delivery of a dose and/or when the arm 1108 is being extended), then the length of the arm 1108 (e.g., maximum extension of the arm 1108) can restrict the amount by which the rack 1102 and the plunger 1104 can move. As a result, delivery of any further drug can be prevented.

Figure 16:
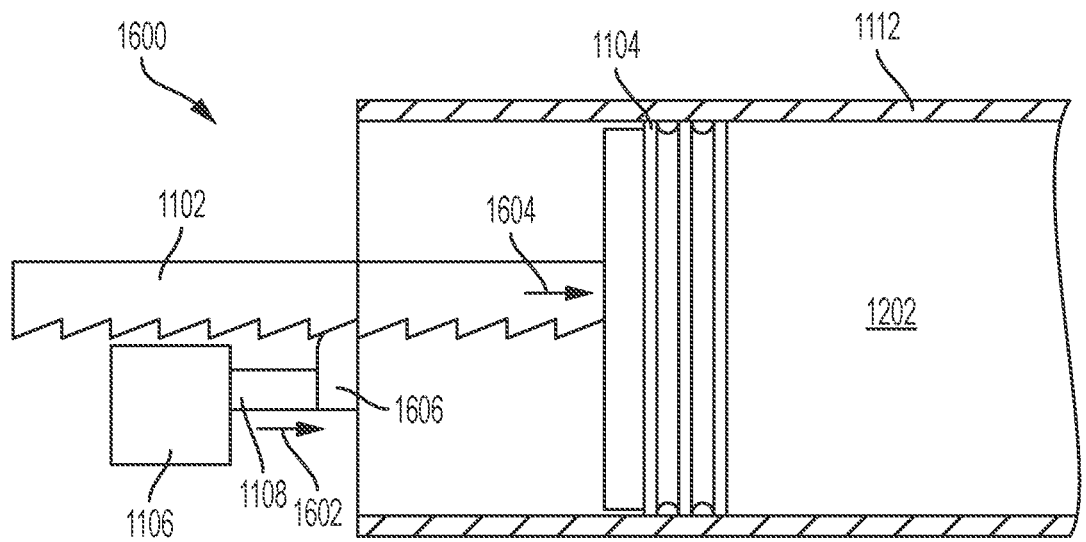
FIG. 16 illustrates a fourth ratchet drive system during delivery of a drug.

FIG. 16 illustrates a fourth exemplary ratchet drive system 1600. The ratchet drive system 1600 can be a variation of the ratchet drive system 1100. As with the ratchet drive systems 100, 800, and 1100, the ratchet drive system 1600 can be used in an OBDS as described herein and can provide the same benefits as the ratchet drive system 1600. The ratchet drive system 1600 can include the rack 1102, the plunger 1104, the power source 1106, the arm 1108, a pawl 1606, and the drug container 1112. The ratchet drive system 1600 can operate in a substantially similar manner as the ratchet system 1100 with the exceptions described herein.

As shown in FIG. 16, the pawl 1606 can be coupled to the arm 1108. As opposed to rotating like the pawl 1110, the pawl 1606 can be coupled to the arm 1108 and arranged to move up and down (e.g., towards and away from the rack 1102) to engage and disengage from the rack 1102 as described further herein.

FIG. 16 illustrates the ratchet drive system 1600 during delivery of the liquid drug. As shown in FIG. 16, the arm 1108 extends in a direction 1602 and the pawl 1606 is engaged with the rack 1102. As a result, the rack 1102 and the plunger 1104 are advanced in a direction 1604 as shown. The advancement of the plunger 1104 further into the drug container 1112 can cause a portion of the liquid drug stored in the reservoir 1202 to be expelled from the drug container 1112 as described above in relation to the ratchet drive system 1100. Once the arm 1108 is extended by a desired or predetermined amount, the arm 1108 and the rack 1102 can come to rest.

Figure 17:
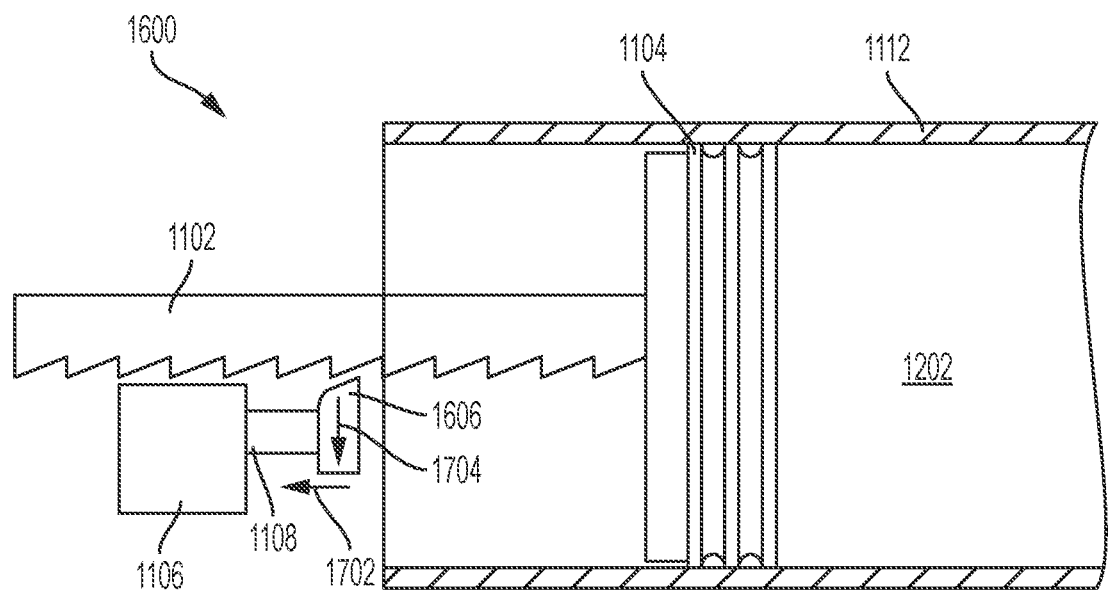
FIG. 17 illustrates the fourth ratchet drive system after delivery of the drug during a first phase of reset.

FIG. 17 illustrates the ratchet drive system 1600 initiating a return to its initial or idle state. As shown in FIG. 17, the arm 1108 is moved in a direction 1702 back toward the power source 1106. The pawl 1606 can move downward in a direction 1704 as the arm 1108 is moved in the direction 1702. As a result, the pawl 1606 is disengaged from the rack 1102. The rack 1102 therefore does not move and remains stationary as the arm 1108 is moved backwards (e.g., in the direction 1702). In various embodiments, the movement of the pawl 1606 in the direction 1704 can be passive, for example, based on a shape of the pawl 1606 and interaction with the teeth of the rack 1102. In various embodiments, the pawl 1606 can be spring loaded to enable disengagement and re-engagement of the pawl 1606 with the rack. In various embodiments, the pawl 1606 can be controlled, for example by a power source, to move in the direction 1704.

Figure 18:
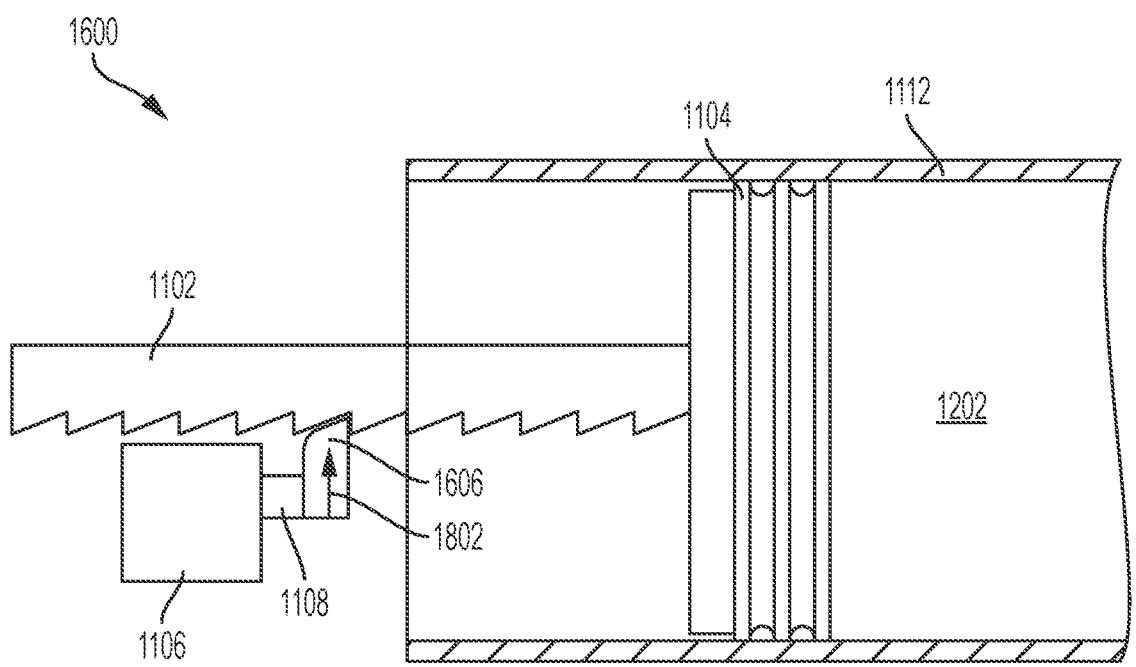
FIG. 18 illustrates the fourth ratchet drive system during a second phase of reset.

FIG. 18 illustrates the ratchet drive system 1600 re-engaging the rack 1102. As shown in FIG. 18, the arm 1108 is in close proximity to the power source 1106. When the arm 1108 stops moving, the pawl 1606 can move upwards in a direction 1802 to re-engage the rack 1102. Once the pawl 1606 re-engages the rack 1102, the ratchet drive system 1600 can be re-activated to a deliver a subsequent predetermined amount of the liquid drug. As described above, the movement of the pawl 1606 (e.g., in the direction 1802) can be passive movement or can be actively controlled.

The following examples pertain to additional embodiments:

Example 1 is a ratchet drive system comprising a ratchet gear, a lead screw coupled to the ratchet gear, an end of the lead screw coupled to a plunger positioned in a drug container, a ratchet carrier positioned around the ratchet gear, a first pawl coupled to the ratchet carrier and a second pawl coupled to the ratchet carrier, the first and second pawls configured to selectively engage the ratchet gear, and a first carrier stop configured to restrict rotation of the ratchet carrier in a first direction.

Example 2 is an extension of Example 1 or any other example disclosed herein, comprising a second carrier stop configured to restrict rotation of the ratchet carrier in a second, opposite direction.

Example 3 is an extension of Example 2 or any other example disclosed herein, wherein the first and second pawls are configured to engage the ratchet gear when the ratchet carrier is rotated in the first direction, thereby coupling the ratchet carrier to the ratchet gear.

Example 4 is an extension of Example 3 or any other example disclosed herein, wherein the ratchet gear and the lead screw are configured to rotate in the first direction when the ratchet carrier is rotated in the first direction.

Example 5 is an extension of Example 4 or any other example disclosed herein, wherein the lead screw is configured to move in a linear direction when the ratchet carrier is rotated in the first direction, the linear direction parallel to an axis of rotation of the ratchet carrier.

Example 6 is an extension of Example 5 or any other example disclosed herein, wherein the lead screw is configured to move the plunger in the linear direction and further into the drug container when the ratchet carrier is rotated in the first direction.

Example 7 is an extension of Example 6 or any other example disclosed herein, wherein the plunger is configured to expel a portion of a liquid drug stored in the drug container when moved in the linear direction.

Example 8 is an extension of Example 7 or any other example disclosed herein, wherein a predetermined dose of the liquid drug is expelled from the drug container when the ratchet carrier is rotated in the first direction from an initial position corresponding to the second carrier stop to a final position corresponding to the first carrier stop.

Example 9 is an extension of Example 8 or any other example disclosed herein, wherein the first and second carrier stops are displaced by approximately 180 degrees.

Example 10 is an extension of Example 8 or any other example disclosed herein, wherein the first carrier stop is configured to prevent the ratchet carrier from rotating further in the first direction.

Example 11 is an extension of Example 8 or any other example disclosed herein, wherein the first and second pawls are configured to disengage the ratchet gear when the ratchet carrier is rotated in the second direction, thereby decoupling the ratchet gear from the ratchet carrier.

Example 12 is an extension of Example 11 or any other example disclosed herein, wherein the ratchet gear and the lead screw are configured to remain stationary when the ratchet gear is rotated in the second direction.

Example 13 is an extension of Example 11 or any other example disclosed herein, wherein the ratchet carrier is rotated in the second direction to return to the initial position to reset the ratchet drive system.

Example 14 is an extension of Example 13 or any other example disclosed herein, wherein the first and second pawls are configured to re-engage the ratchet gear when the ratchet drive system is reset.

Example 15 is an extension of Example 13 or any other example disclosed herein, further comprising a power source for rotating the ratchet carrier.

Example 16 is an extension of Example 51 or any other example disclosed herein, wherein the ratchet gear comprises gear teeth position around a perimeter of the ratchet carrier, wherein the ratchet drive system further comprises a gear coupled to the gear teeth of the ratchet carrier and coupled to the power source, wherein the power source rotates the ratchet carrier by rotating the gear.

Example 17 is an extension of Example 16 or any other example disclosed herein, further comprising a controller, the controller configured to control operation of the power source and rotation of the ratchet carrier.

Example 18 is an extension of Example 17 or any other example disclosed herein, wherein the first and second carrier stops each include a sensor configured to detect when the ratchet carrier is in the final position and the initial position, respectively.

Example 19 is an extension of Example 18 or any other example disclosed herein, wherein each sensor is configured to transmit a signal to the controller to indicate at least one of the final position and the initial position of the ratchet carrier.

Example 20 is an extension of Example 18 or any other example disclosed herein, wherein the controller is configured to maintain a count of a number of predetermined doses of the liquid drug that have been delivered based on the signals transmitted by the sensors.

Example 21 is an extension of Example 1 or any other example disclosed herein, wherein the drive system is part of an on-body delivery system (OBDS).

Example 22 is a method comprising rotating a ratchet carrier in a first direction from an initial position to a final position, rotating a ratchet gear in the first direction based on rotating the ratchet carrier, rotating a lead screw in the first direction based on rotating the ratchet gear, moving the lead screw in a linear direction parallel to an axis of rotation of the lead screw based on rotating the lead screw, the lead screw coupled to a plunger positioned in a drug container holding a liquid drug, and moving the plunger in the linear direction further into the drug container based on moving the lead screw, thereby expelling a dose of the liquid drug from the drug container.

Example 23 is an extension of Example 22 or any other example disclosed herein, further comprising restricting rotation of the ratchet carrier beyond the final position based on a position of a first carrier stop.

Example 24 is an extension of Example 23 or any other example disclosed herein, further comprising detecting the final position of the ratchet carrier based on a sensor of the first carrier stop.

Example 25 is an extension of Example 24 or any other example disclosed herein, further comprising maintaining a count of a number of doses of the liquid drug expelled based on detecting the final position of the ratchet carrier.

Example 26 is an extension of Example 25 or any other example disclosed herein, further comprising rotating the ratchet gear in a second direction opposite the first direction from the final position to the initial position.

Example 27 is an extension of Example 26 or any other example disclosed herein, further comprising decoupling the ratchet carrier from the ratchet gear prior to rotating the ratchet gear in the second direction, thereby preventing the ratchet gear and the lead screw from rotating in the second direction.

Example 28 is an extension of Example 27 or any other example disclosed herein, further comprising restricting rotation of the ratchet carrier beyond the initial position based on a position of a second carrier stop.

Example 29 is an extension of Example 28 or any other example disclosed herein, further comprising detecting the initial position of the ratchet carrier based on a sensor of the second carrier stop.

The following examples pertain to further additional embodiments:

Example 1 is a ratchet drive system, comprising a power source, an arm coupled to the power source, a pawl coupled to an end of the arm, a rack coupled to the arm through the pawl, and a plunger coupled to the end of the rack, the plunger positioned within a drug container storing a liquid drug.

Example 2 is an extension of Example 1 or any other example disclosed herein, the power source configured to cause the arm to extend in a first direction, thereby moving the rack in the first direction.

Example 3 is an extension of Example 2 or any other example disclosed herein, wherein the plunger is configured move in the first direction further into the drug container when the rack is moved in the first direction.

Example 4 is an extension of Example 3 or any other example disclosed herein, wherein a portion of the liquid drug is expelled from the drug container when the plunger is moved in the first direction.

Example 5 is an extension of Example 4 or any other example disclosed herein, wherein a predetermined dose of the liquid drug is expelled from the drug container when the arm is moved in the first direction from an initial position to a final position.

Example 6 is an extension of Example 5 or any other example disclosed herein, wherein the final position corresponds to a maximum extension of the arm.

Example 7 is an extension of Example 6 or any other example disclosed herein, wherein the pawl is configured to disengage the rack after the arm is in the final position.

Example 8 is an extension of Example 7 or any other example disclosed herein, wherein the power source is configured to cause the arm to move in a second, opposite direction after the arm is in the final position.

Example 9 is an extension of Example 8 or any other example disclosed herein, wherein the rack and the plunger are configured to remain stationary when the arm moves in the second direction.

Example 10 is an extension of Example 9 or any other example disclosed herein, wherein the ratchet drive system is reset when the arm moves in the second direction to return to the initial position.

Example 11 is an extension of Example 10 or any other example disclosed herein, wherein the pawl is configured to re-engage the rack when the ratchet drive system is reset.

Example 12 is an extension of Example 11 or any other example disclosed herein, further comprising a controller for activating movement of the arm in the first direction and the second direction based on control of the power source.

Example 13 is an extension of Example 12 or any other example disclosed herein, wherein the power source is a motor.

Example 14 is an extension of Example 12 or any other example disclosed herein, wherein the power source is a linear actuator.

Example 15 is an extension of Example 12 or any other example disclosed herein, wherein the controller is configured to maintain a count of a number of predetermined doses of the liquid drug that have been expelled based on the movement of the arm.

Example 16 is an extension of Example 1 or any other example disclosed herein, wherein the drive system is part of an on-body delivery system (OBDS).

Example 17 is a method comprising extending an arm in a first direction from an initial position to a final position, moving a rack in the first direction based on extending the arm, the rack coupled to a plunger positioned in a drug container holding a liquid drug, and moving the plunger in the first direction further into the drug container based on moving the rack, thereby expelling a dose of the liquid drug from the drug container.

Example 18 is an extension of Example 17 or any other example disclosed herein, further comprising detecting the final position of the arm.

Example 19 is an extension of Example 18 or any other example disclosed herein, further comprising maintaining a count of a number of doses of the liquid drug expelled based on detecting the final position of the arm.

Example 20 is an extension of Example 19 or any other example disclosed herein, further comprising coupling the arm to the rack with a pawl.

Example 21 is an extension of Example 20 or any other example disclosed herein, further comprising moving the pawl to decouple the arm from the rack after the arm is extended to its final position.

Example 22 is an extension of Example 21 or any other example disclosed herein, further comprising rotating the pawl to decouple the arm from the rack after the arm is extended to its final position.

Example 23 is an extension of Example 21 or any other example disclosed herein, further comprising moving the pawl in a direction away from the rack to decouple the arm from the rack after the arm is extended to its final position.

Example 24 is an extension of Example 21 or any other example disclosed herein, further comprising moving the arm in a second direction opposite the first direction to retract the arm to the initial position from the final position.

Example 25 is an extension of Example 24 or any other example disclosed herein, further comprising restricting movement of the rack and the plunger in the second direction.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A system, comprising: a ratchet gear; a lead screw coupled to the ratchet gear, an end of the lead screw coupled to a plunger positioned in a drug container; a ratchet carrier positioned around the ratchet gear, wherein the ratchet carrier includes an extension extending from a perimeter of the ratchet carrier; a first pawl coupled to the ratchet carrier and a second pawl coupled to the ratchet carrier, the first and second pawls configured to selectively engage the ratchet gear; and a first carrier stop configured to restrict rotation of the ratchet carrier in a first direction by stopping the extension from further rotation in the first direction; and a second carrier stop configured to restrict rotation of the ratchet carrier in a second, opposite direction by coming into contact with and stopping the extension from further rotation in the second, opposite direction.

2. The system of claim 1, wherein the first and second pawls are configured to engage the ratchet gear when the ratchet carrier is rotated in the first direction, thereby coupling the ratchet carrier to the ratchet gear.

3. The system of claim 2, wherein the ratchet gear and the lead screw are configured to rotate in the first direction when the ratchet carrier is rotated in the first direction.

4. The system of claim 3, wherein the lead screw is configured to move in a linear direction when the ratchet carrier is rotated in the first direction, the linear direction parallel to an axis of rotation of the ratchet carrier.

5. The system of claim 4, wherein the lead screw is configured to move the plunger in the linear direction and further into the drug container when the ratchet carrier is rotated in the first direction.

6. The system of claim 5, wherein the plunger is configured to expel a portion of a liquid drug stored in the drug container when moved in the linear direction.

7. The system of claim 6, wherein a predetermined dose of the liquid drug is expelled from the drug container when the ratchet carrier is rotated in the first direction from an initial position corresponding to the second carrier stop to a final position corresponding to the first carrier stop.

8. The system of claim 7, wherein the first carrier stop is configured to prevent the ratchet carrier from rotating further in the first direction.

9. The system of claim 7, wherein the first and second pawls are configured to disengage the ratchet gear when the ratchet carrier is rotated in the second direction, thereby decoupling the ratchet gear from the ratchet carrier.

10. The system of claim 9, wherein the ratchet gear and the lead screw are configured to remain stationary when the ratchet carrier is rotated in the second direction.

11. The system of claim 9, wherein the ratchet carrier is rotated in the second direction to return to the initial position to reset the ratchet drive system.

12. The system of claim 11, wherein the first and second pawls are configured to re-engage the ratchet gear when the ratchet drive system is reset.

13. The system of claim 12, further comprising a controller, the controller configured to control operation of a power source for rotating the ratchet carrier.

14. The system of claim 13, wherein the first and second carrier stops each include a sensor configured to detect when the ratchet carrier is in the final position and the initial position, respectively.

15. The system of claim 14, wherein each sensor is configured to transmit a signal to the controller to indicate at least one of the final position and the initial position of the ratchet carrier.

16. The system of claim 15, wherein the controller is configured to maintain a count of a number of predetermined doses of the liquid drug that have been delivered based on the signals transmitted by the sensors.

17. A method, comprising:
rotating a ratchet carrier in a first direction from an initial position to a final position;
rotating a ratchet gear in the first direction based on rotating the ratchet carrier;
rotating a lead screw in the first direction based on rotating the ratchet gear;
moving the lead screw in a linear direction parallel to an axis of rotation of the lead screw based on rotating the lead screw, the lead screw coupled to a plunger positioned in a drug container holding a liquid drug;
moving the plunger in the linear direction further into the drug container based on moving the lead screw, thereby expelling a dose of the liquid drug from the drug container;
decoupling the ratchet carrier from the ratchet gear; and
rotating the ratchet carrier in a second direction opposite the first direction from the final position to the initial position, wherein decoupling the ratchet carrier from the ratchet gear prior to rotating the ratchet gear in the second direction prevents the ratchet gear and the lead screw from rotating in the second direction.

18. The method of claim 17, further comprising restricting rotation of the ratchet carrier beyond the final position based on a position of a first carrier stop.

19. The method of claim 18, further comprising detecting the final position of the ratchet carrier based on a sensor of the first carrier stop.

20. The method of claim 19, further comprising maintaining a count of a number of doses of the liquid drug expelled based on detecting the final position of the ratchet carrier.

21. The method of claim 18, further comprising restricting rotation of the ratchet carrier beyond the initial position based on a position of a second carrier stop.

22. The method of claim 21, further comprising detecting the initial position of the ratchet carrier based on a sensor of the second carrier stop.

* * * * *

UNITED STATES PATENT AND TRADEMARK OFFICE
CERTIFICATE OF CORRECTION

PATENT NO. : 10,780,217 B2
APPLICATION NO. : 15/809491
DATED : September 22, 2020
INVENTOR(S) : Nazzaro et al.

Page 1 of 1

It is certified that error appears in the above-identified patent and that said Letters Patent is hereby corrected as shown below:

In the Claims

Column 15, Claim 1, Line 22; Please remove "and" before "a first carrier..."

Signed and Sealed this
Tenth Day of November, 2020

Andrei Iancu
*Director of the United States Patent and Trademark Office*